US011623960B2

(12) United States Patent
Shih et al.

(10) Patent No.: US 11,623,960 B2
(45) Date of Patent: Apr. 11, 2023

(54) DUAL-FUNCTION ANTIBODIES TARGETING VEGFR2 AND VEGFR3

(71) Applicant: National Health Research Institutes, Miaoli County (TW)

(72) Inventors: Neng-yao Shih, Miaoli County (TW); Ko-jiunn Liu, Miaoli County (TW); Li-tzong Chen, Miaoli County (TW); Wen-chun Hung, Miaoli County (TW); Yun-chang Chen, Miaoli County (TW); Kuan-chung Hsiao, Miaoli County (TW); San-tai Shen, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 88 days.

(21) Appl. No.: 16/982,361

(22) PCT Filed: Mar. 20, 2019

(86) PCT No.: PCT/US2019/023099
§ 371 (c)(1),
(2) Date: Sep. 18, 2020

(87) PCT Pub. No.: WO2019/183177
PCT Pub. Date: Sep. 26, 2019

(65) Prior Publication Data
US 2021/0032353 A1      Feb. 4, 2021

Related U.S. Application Data

(60) Provisional application No. 62/645,437, filed on Mar. 20, 2018.

(51) Int. Cl.
*A61K 39/395* (2006.01)
*C07K 16/28* (2006.01)
*A61P 35/00* (2006.01)
*A61K 39/00* (2006.01)

(52) U.S. Cl.
CPC .......... *C07K 16/2863* (2013.01); *A61P 35/00* (2018.01); *A61K 2039/505* (2013.01); *C07K 2317/24* (2013.01); *C07K 2317/565* (2013.01); *C07K 2317/73* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 2010/0035280 A1 | 2/2010 | Kawai |
| 2017/0096479 A1 | 4/2017 | Koenig et al. |
| 2017/0129942 A1 | 5/2017 | Plante et al. |

FOREIGN PATENT DOCUMENTS

WO   WO-2017/004254 A1   1/2017

OTHER PUBLICATIONS

Dondelinger et al. (Frontiers in Immunology, vol. 9, Article 2278, 2018).*
Koichi Hamada, et al. "VEGF-C signaling pathways through VEGFR-2 and VEGFR-3 in vasculoangiogenesis and hematopoiesis." Blood. Dec. 1, 2000. vol. 96, No. 12. pp. 3793-3800.
Xenia Jimenez, et al. "A recombinant, fully human, bispecific antibody neutralizes the biological activities mediated by both vascular endothelial growth factor receptors 2 and 3." Molecular Cancer Therapies. Mar. 1, 2005. vol. 4, No. 3. pp. 427-434.
Annette Orleth, et al. "Simultaneous targeting of VEGF-receptors 2 and 3 with immunoliposomes enhances therapeutic efficacy." Journal of Drug Targeting. Jul. 23, 2015. vol. 24, No. 1. pp. 80-89.
Ingo Schubert, et al. "Dual-Targeting for the Elimination of Cancer Cells with Increased Selectivity." Antibodies. Apr. 10, 2012. vol. 1, No. 1. pp. 2-18.
Falcon et al "Antagonist Antibodies to Vascular Endothelial Growth Factor Receptor 2 (VEGFR-2) as Anti-Angiogenic Agents" Pharmacology and Therapeutics vol. 164, pp. 204-225, 2016.
Kendrew et al "An Antibody Targeted to VEGFR-2 Ig Domains 4-7 Inhibits VEGFR-2 Activation and VEGFR-2-Depenent Angiogenesis Without Affecting Ligand Binding" Molecular Cancer Therapeutics vol. 10, pp. 770-783, 2011.
McDonald "New Antibody to Stop Tumor Angiogenesis and Lymphatic Spread by Blocking Receptor Partnering" Cancer Cell vol. 18, pp. 541-543, 2010.
Smith et al "Vascular Endothelial Growth Factor Receptors VEGFR-2 and VEGFR-3 are Localized Primarily to the Vasculature in Human Primary Solid Cancers" Clinical Cancer Research vol. 16, pp. 3548-3561, 2010.
Tvorogov et al "Effective Suppression of Vascular Network Formation by Combination of Antibodies Blocking VEGFR Ligand Binding and Receptor Dimerization" Cancer Cell vol. 18, pp. 630-640, 2010.

* cited by examiner

*Primary Examiner* — Christine J Saoud
(74) *Attorney, Agent, or Firm* — Cesari & McKenna, LLP

(57) ABSTRACT

An isolated antibody, comprising heavy chain complementary determining regions CDR1, CDR2, and CDR3 from a heavy chain variable region sequence having SEQ ID NO: 1 or 3; light chain complementary determining regions CDR1, CDR2, and CDR3 from a light chain variable region sequence having SEQ ID NO: 2 or 4; wherein the antibody binds specifically to both vascular endothelial growth factor receptor-2 (VEGFR2) and vascular endothelial growth factor receptor-3 (VEGFR3).

16 Claims, 11 Drawing Sheets
Specification includes a Sequence Listing.

SEQUENCE LISTING

<160> NUMBER OF SEQ ID NOS: 20

<210> SEQ ID NO 1
<211> LENGTH: 117
<212> TYPE: PRT
<213> ORGANISM: Artificial Sequence
<220> FEATURE:
<223> OTHER INFORMATION: R2C7-1 VH

<400> SEQUENCE: 1

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Phe Ile Asn Trp Val Ile Gln Arg His Gly Lys Ser Leu Glu Trp Val
        35                  40                  45

Gly Arg Ile Asn Pro Tyr Asn Gly Gly Ser Phe Tyr Asn Gln Lys Phe
    50                  55                  60

Lys Asp Lys Ala Thr Leu Thr Val Asp Lys Ser Ser Asn Ile Ala His
65                  70                  75                  80

Met Glu Leu Arg Ser Leu Ala Ser Glu Asp Ser Ala Ile Tyr Tyr Cys
                85                  90                  95

Ala Arg Ser Gly Gly Asn Gly Tyr Asp Tyr Trp Gly Gln Gly Thr Thr
            100                 105                 110

Leu Thr Val Ser Ser
        115
```

<210> SEQ ID NO 2
<211> LENGTH: 112
<212> TYPE: PRT
<213> ORGANISM: Artificial Sequence
<220> FEATURE:
<223> OTHER INFORMATION: R2C7-1 VL

<400> SEQUENCE: 2

```
Asp Ile Val Met Thr Gln Ala Ala Pro Ser Val Pro Val Ile Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95
```

```
Leu Glu Tyr Pro Tyr Thr Phe Gly Gly Gly Thr Lys Val Glu Ile Lys
            100                 105                 110
```

<210> SEQ ID NO 3
<211> LENGTH: 114
<212> TYPE: PRT
<213> ORGANISM: Artificial Sequence
<220> FEATURE:
<223> OTHER INFORMATION: R2C9-11 VH

<400> SEQUENCE: 3

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Leu Tyr Phe Asp Val Trp Gly Ala Gly Thr Thr Val Thr Val
            100                 105                 110

Ser Ser
```

<210> SEQ ID NO 4
<211> LENGTH: 113
<212> TYPE: PRT
<213> ORGANISM: Artificial Sequence
<220> FEATURE:
<223> OTHER INFORMATION: R2C9-11 VL

<400> SEQUENCE: 4

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Asn Leu Leu Asn Ser
            20                  25                  30

Gly Asn Gln Lys Tyr Tyr Leu Ala Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Phe Cys Gln Ser
                85                  90                  95

Asp His Ser Tyr Pro Tyr Thr Phe Gly Gly Gly Thr Lys Leu Glu Ile
            100                 105                 110

Lys
```

<210> SEQ ID NO 5
<211> LENGTH: 5
<212> TYPE: PRT
<213> ORGANISM: Artificial Sequence
<220> FEATURE:
<223> OTHER INFORMATION: R2C7-1 VH CDR-1; Kabat

```
<400> SEQUENCE: 5

Asp Tyr Phe Ile Asn
1               5

<210> SEQ ID NO 6
<211> LENGTH: 17
<212> TYPE: PRT
<213> ORGANISM: Artificial Sequence
<220> FEATURE:
<223> OTHER INFORMATION: R2C7-1 VH CDR-2; Kabat

<400> SEQUENCE: 6

Arg Ile Asn Pro Tyr Asn Gly Gly Ser Phe Tyr Asn Gln Lys Phe Lys
1               5                   10                  15

Asp

<210> SEQ ID NO 7
<211> LENGTH: 8
<212> TYPE: PRT
<213> ORGANISM: Artificial Sequence
<220> FEATURE:
<223> OTHER INFORMATION: R2C7-1 VH CDR-3

<400> SEQUENCE: 7

Ser Gly Gly Asn Gly Tyr Asp Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: R2C7-1 VH CDR-1; Chothia

<400> SEQUENCE: 8

Gly Tyr Ser Phe Thr Asp Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: R2C7-1 VH CDR-2; Chothia

<400> SEQUENCE: 9

Asn Pro Tyr Asn Gly Gly
1               5

<210> SEQ ID NO 10
<211> LENGTH: 16
<212> TYPE: PRT
<213> ORGANISM: Artificial Sequence
<220> FEATURE:
<223> OTHER INFORMATION: R2C7-1 VL CDR-1

<400> SEQUENCE: 10

Arg Ser Ser Lys Ser Leu Leu His Ser Asn Gly Asn Thr Tyr Leu Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: R2C7-1 VL CDR-2
```

<400> SEQUENCE: 11

Arg Met Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: R2C7-1 VL CDR-3

<400> SEQUENCE: 12

Met Gln His Leu Glu Tyr Pro Tyr Thr
1               5

<210> SEQ ID NO 13
<211> LENGTH: 5
<212> TYPE: PRT
<213> ORGANISM: Artificial Sequence
<220> FEATURE:
<223> OTHER INFORMATION: R2C9-11 VH CDR-1; Kabat

<400> SEQUENCE: 13

Ser Tyr Trp Met His
1               5

<210> SEQ ID NO 14
<211> LENGTH: 17
<212> TYPE: PRT
<213> ORGANISM: Artificial Sequence
<220> FEATURE:
<223> OTHER INFORMATION: R2C9-11 VH CDR-2; Kabat

<400> SEQUENCE: 14

Glu Ile Asn Pro Ser Asn Gly Arg Thr Asn Tyr Asn Glu Lys Phe Lys
1               5                   10                  15

Ser

<210> SEQ ID NO 15
<211> LENGTH: 5
<212> TYPE: PRT
<213> ORGANISM: Artificial Sequence
<220> FEATURE:
<223> OTHER INFORMATION: R2C9-11 VH CDR-3

<400> SEQUENCE: 15

Leu Tyr Phe Asp Val
1               5

<210> SEQ ID NO 16
<211> LENGTH: 7
<212> TYPE: PRT
<213> ORGANISM: Artificial Sequence
<220> FEATURE:
<223> OTHER INFORMATION: R2C9-11 VH CDR-1; Chothia

<400> SEQUENCE: 16

Gly Tyr Thr Phe Thr Ser Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: R2C9-11 VH CDR-2; Chothia

```
<400> SEQUENCE: 17

Asn Pro Ser Asn Gly Arg
1               5

<210> SEQ ID NO 18
<211> LENGTH: 17
<212> TYPE: PRT
<213> ORGANISM: Artificial Sequence
<220> FEATURE:
<223> OTHER INFORMATION: R2C9-11 VL CDR-1

<400> SEQUENCE: 18

Lys Ser Ser Gln Asn Leu Leu Asn Ser Gly Asn Gln Lys Tyr Tyr Leu
1               5                   10                  15

Ala

<210> SEQ ID NO 19
<211> LENGTH: 7
<212> TYPE: PRT
<213> ORGANISM: Artificial Sequence
<220> FEATURE:
<223> OTHER INFORMATION: R2C9-11 VL CDR-2

<400> SEQUENCE: 19

Gly Ala Ser Ile Arg Glu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: R2C9-11 VL CDR-3

<400> SEQUENCE: 20

Gln Ser Asp His Ser Tyr Pro Tyr Thr
1               5
```

DUAL-FUNCTION ANTIBODIES TARGETING VEGFR2 AND VEGFR3

CROSS-REFERENCE TO RELATED APPLICATION

This application is the National Stage of International Application No. PCT/US2019/023099, filed on Mar. 20, 2019, which claims priority to U.S. Provisional Application No. 62/645,437, filed on Mar. 20, 2018, the contents of both prior applications being hereby incorporated by reference in their entirety.

BACKGROUND

Angiogenesis and lymphangiogenesis are essential for tumor development and highly associated with disease malignancy. Biological activity all depends on the binding of vascular endothelial growth factors (VEGFs) to their corresponding receptors (VEGFRs) and in turn, to induce receptor dimerization, autophosphorylation, and activation of the downstream signaling. The consequent action leads to cell proliferation, cell migration, vascular permeability, and neovascular survival. See, Olsson et al., Nat Rev Mol Cell Biol, 2006. 7(5): p. 359-71. VEGF-A and VEGF-C are considered as the major VEGF ligands responsible for angiogenesis and lymphangiogenesis. In previous pre-clinical studies, blockade of effector binding to its receptor, VEGFR2 or VEGFR3, has been shown to lead to a remarkable inhibition of tumor growth. However, treatment with the monoclonal antibody bevacizumab (Avastin) to block VEGF-A only delayed progression and prolonged survival in some cancers. See, Mukherji, S. K., AJNR Am J Neuroradiol, 2010. 31(2): p. 235-6; and Bagri, A., et al., Trends Mol Med, 2010. 16(3): p. 122-32. The major factor causing clinical failure in tumor malignancy is unable to slow the growth of lymphatic vessels (lymphangiogenesis) that serve as routes for cancer cells to spread to lymph nodes and distant sites. See, McDonald, D. M., Cancer Cell, 2010. 18(6): p. 541-3. Thus, selective inhibitors of lymphangiogenesis would complement angiogenesis inhibitors; however, none is yet available for clinical use.

Currently, three strategies to block VEGFR signaling activation have been developed. Beside bevacizumab as an antiangiogenic ligand by cytostatic mechanism of action, aflibercept, a chimeric decoy receptor that binds VEGF, is in advanced clinical trials. See, Ellis, L. M., Semin Oncol, 2006. 33(5 Suppl 10): p. S1-7; and Holash, J., et al., Proc Natl Acad Sci USA, 2002. 99(17): p. 11393-8. A second class of inhibitor belongs to small molecules to inhibit the intracellular tyrosine kinase activity of VEGFRs such as PTK787, Sutent, sorafinib, Zactima, and Recentin. See, Wedge, S. R., et al., Cancer Res, 2002. 62(16): p. 4645-55; Wedge, S. R., et al., Cancer Res, 2005. 65(10): p. 4389-400; Wood, J. M., et al., Cancer Res, 2000. 60(8): p. 2178-89; Mendel, D. B., et al., Clin Cancer Res, 2003. 9(1): p. 327-37; and Wilhelm, S. M., et al., Cancer Res, 2004. 64(19): p. 7099-109. Other macromolecular therapeutics, including Ramucirumab (Cyramza) and CDP-791, are used to block the interaction of VEGF-A with VEGFR-2. See, Krupitskaya, Y. and H. A. Wakelee, Curr Opin Investig Drugs, 2009. 10(6): p. 597-605; and Lu, D., et al., J Biol Chem, 2003. 278(44): p. 43496-507. These agents are selective, well tolerated, and generally have only modest side effects restricted to consequences of inhibiting VEGF in normal organs.

VEGF receptor (VEGFR) is a broader family of receptor tyrosine kinases, consisting of VEGFR1, 2, and 3, also known as Flt-1, KDR, and Flt-4, respectively. The structure and functional domains of this family are highly similar, containing 7 extracellular immunoglobin-like (Ig) domains for ligand binding, transmembrane domain for cell-surface docking, and a dual tyrosine kinase domain for receptor trans-autophosphorylation. Ligands such as VEGF-A and placental growth factor bind to the VEGFRs within Ig domains 2 and 3, with domain 2 making the primary contact and domain 3 determining the specificity of binding. See, Christinger, H. W., et al., J Biol Chem, 2004. 279(11): p. 10382-8; Fuh, G., et al., J Biol Chem, 1998. 273(18): p. 11197-204. In contrast, Ig domains 4-6 are involved in dimerization of the receptor complexes.

Since receptor dimerization and transphosphorylation are required to generate sustained downstream signaling in theory, receptor mediated angiogenic or lymphangiogenic activity can be inhibited by inhibiting ligand-receptor binding or by blocking dimerization.

Notably, blockade of VEGFR-2 signaling through inhibition of dimerization not only prevent VEGFR2 and VEGFR3 homodimerization, but also interferes with VEGFR2/VEGFR3 heterodimerization. Hence, this strategy can be a novel mechanism potentially for simultaneous inhibition of VEGFR2- and VEGFR3-mediated signalings, resulting in suppression of tumor growth and tumor spread.

SUMMARY

In one aspect, described herein is an isolated antibody, comprising heavy chain complementary determining regions CDR1, CDR2, and CDR3 from a heavy chain variable region sequence having SEQ ID NO: 1 or 3; and light chain complementary determining regions CDR1, CDR2, and CDR3 from a light chain variable region sequence having SEQ ID NO: 2 or 4; wherein the antibody binds specifically to both vascular endothelial growth factor receptor-2 (VEGFR2) and vascular endothelial growth factor receptor-3 (VEGFR3).

In some embodiments, the heavy chain CDR1, CDR2, and CDR3 are from SEQ ID NO: 1, and the light chain CDR1, CDR2, and CDR3 are from SEQ ID NO: 2. The antibody can include a heavy chain variable region that is at least 80% (e.g., 80%, 85%, 90%, 95%, 96%, 97%, 98%, 99%, or 100%) identical to the sequence of SEQ ID NO: 1, and a light chain variable region that is at least 80% (e.g., 85%, 90%, 95%, 96%, 97%, 98%, 99%, or 100%) identical to the sequence of SEQ ID NO: 2.

In some embodiments, the heavy chain CDR1 has SEQ ID NO: 5 or 8, the heavy chain CDR2 has SEQ ID NO: 6 or 9, and the heavy chain CDR3 has SEQ ID NO: 7, and wherein the light chain CDR1, CDR2, and CDR3, respectively, have SEQ ID NO: 10, 11, and 12.

In some embodiments, the heavy chain CDR1, CDR2, and CDR3 are from SEQ ID NO: 3, and the light chain CDR1, CDR2, and CDR3 are from SEQ ID NO: 4. The antibody can include a heavy chain variable region that is at least 80% (e.g., 85%, 90%, 95%, 96%, 97%, 98%, 99%, or 100%) identical to the sequence of SEQ ID NO: 3, and a light chain variable region that is at least 80% (e.g., 85%, 90%, 95%, 96%, 97%, 98%, 99%, or 100%) identical to the sequence of SEQ ID NO: 4.

In some embodiments, the heavy chain CDR1 has SEQ ID NO: 13 or 16, the heavy chain CDR2 has SEQ ID NO: 14 or 17, and the heavy chain CDR3 has SEQ ID NO: 15, and wherein the light chain CDR1, CDR2, and CDR3, respectively, have SEQ ID NO: 18, 19, and 20.

In some embodiments, the antibody is an antibody that contains an Fc region, an Fab fragment, an Fab' fragment, an F(ab')2 fragment, a single-chain antibody, an scFV multimer, a monovalent antibody, a multispecific antibody, or a chimeric antibody. In some embodiments, the antibody is a humanized antibody.

In another aspect, provided herein is a pharmaceutical composition comprising the antibody described herein and a pharmaceutically acceptable carrier.

In yet another aspect, described herein is an antibody conjugate comprising the antibody described herein and another molecule (e.g., a small molecule drug, a cell-targeting moiety, a cytotoxic agent, a polypeptide, a nucleic acid molecule, a detectable label, or a polymer).

In one aspect, a method of inhibiting homodimerization of VEGFR2 and/or VEGFR3 or heterodimerization of VEGFR2 and VEGFR3 in a cell is described herein. The method comprises contacting the cell with the antibody described herein.

In one aspect, contemplated herein is a method of inhibiting VEGFR2 and/or VEGFR3 signaling in a cell, comprising contacting the cell with the antibody described herein.

In another aspect, provided herein is a method of inhibiting angiogenesis and/or lymphangiogenesis in a subject in need thereof, comprising administering to the subject an effective amount of the antibody described herein.

In yet another aspect, described herein is a method of treating a solid tumor in a subject in need thereof. The method comprises administering to the subject an effective amount of the antibody described herein. In some embodiments, the solid tumor is selected from the group consisting of bladder cancer, breast cancer, cervical cancer, colon cancer, rectal cancer, kidney cancer, liver cancer, skin cancer, mesothelioma, lung cancer, oral cancer, ovarian cancer, pancreatic cancer, prostate cancer, sarcoma, and thyroid cancer. The method can further comprise administering another therapeutic agent to the subject.

In one aspect, provided herein is a method of detecting VEGFR2 and/or VEGFR3 or a fragment thereof in a biological sample, comprising: contacting the sample with the antibody described herein; and assaying for specific binding between the antibody and VEGFR2 and/or VEGFR3 or a fragment thereof.

The details of one or more embodiments are set forth in the accompanying drawing and the description below. Other features, objects, and advantages of the embodiments will be apparent from the description and drawing, and from the claims.

DETAILED DESCRIPTION

Figure 1:
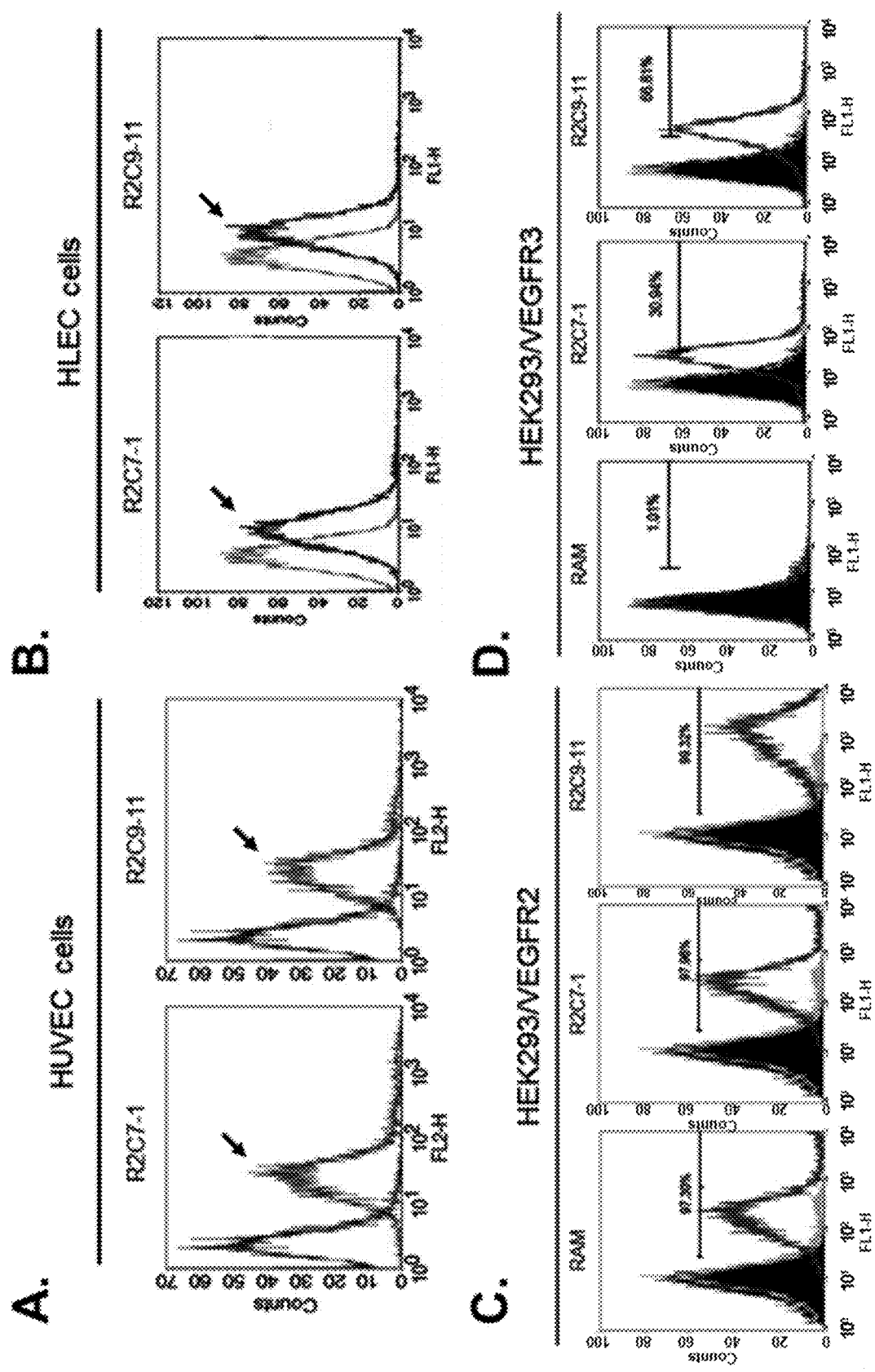
FIG. 1 is a set of flow cytometry histograms to show the recognition of both VEGFR2 and VEGFR3 by R2C7-1 and R2C9-11 monoclonal antibodies (mAbs). Panels A and B, primary human umbilical vein endothelial cells (HUVEC) and human lymphatic endothelial cell (HLEC), respectively. The $3^{rd}$-$6^{th}$ passages of the primary cells were used in experiments. Panels C and D, HEK293T cells overexpressing VEGFR2 (HEK293TNEGFR2) and VEGFR3 (HEK293T/VEGFR3), respectively. HEK293T cells were stably transfected with human VEGFR2 or VEGFR3 genes, as indicated. Those transfectants with high expression of VEGFR2 or VEGFR3 were immuno-selected by antibody against VEGFR2 (Abcam9530) or against VEGFR3 (R&D54703), respectively, using the BD FACSJazz™ cell sorter. Intact primary cells or transfectants ($1\times10^5$ cells/reaction) were stained with R2C7-1 or R2C9-11 (10 µg/mL.; arrow). $IgG_{2a}$ isotype antibody (CTL) served as negative control. Ramucirumab (RAM) (10 µg/mL) was acted as a VEGFR2-positive control. In addition, cells stained with secondary antibody alone were considered as background, and stained-positive cells were expressed as the percentage of total cells (Panels C and D; top).

Described herein are dual-function antibodies that specifically target both vascular endothelial growth factor receptor-2 (VEGFR2) and vascular endothelial growth factor receptor-3 (VEGFR3). The antibodies each can block homodimerization of VEGFR2 and VEGFR3 as well as heterodimerization of the two proteins without affecting ligand binding. Such antibodies can modulate VEGFR2 and VEGFR3 signaling pathways, and inhibit both angiogenesis and lymphangiogenesis.

In some embodiments, the heavy chain complementary determining regions CDR1, CDR2, and CDR3 of the antibody are from a heavy chain variable region sequence having SEQ ID NO: 1 or 3, and the light chain complementary determining regions CDR1, CDR2, and CDR3 are from a light chain variable region sequence having SEQ ID NO: 2 or 4.

In some embodiments, the heavy chain CDR1 can be SEQ ID NO: 5, 8, 13, or 16. The heavy chain CDR2 can be SEQ ID NO: 6, 9, 14, or 17. The heavy chain CDR3 can be SEQ ID NO: 7 or 15. The light chain CDR1 can be SEQ ID NO: 10 or 18. The light chain CDR2 can be SEQ ID NO: 11 or 19. The light chain CDR3 can be SEQ ID NO: 12 or 20.

In some embodiments, the antibody binds to epitopes within domains IgD6 and IgD7 of VEGFR2 and within domain IgD6 of VEGFR3. The epitopes may be structural.

The term "antibody" as used herein includes various antibody structures that have an antigen-binding activity, including but not limited to monoclonal antibodies, polyclonal antibodies, full-length antibodies or fragments thereof, antibodies that contain an Fc region, Fab fragments, Fab' fragments, F(ab')₂ fragments, single-chain antibodies, scFV multimers, monovalent antibodies, multivalent antibodies, humanized antibodies and chimeric antibodies.

The antibody can also be conjugated to another molecule, e.g., a small molecule drug, another protein or peptide, a detection label, a polymer, or a carbohydrate.

Based on the antibody sequences disclosed herein and their CDRs, a skilled practitioner would be able to produce an anti-VEGFR2/anti-VEGFR3 antibody in various forms using methods described herein or known in the art, e.g., recombinant methods.

Also contemplated herein is an isolated nucleic acid molecule (e.g., an expression vector) that encodes the antibody described herein or a component thereof. For example, the nucleic acid molecule can encode any of SEQ ID NOs: 1-20. A host cell containing the nucleic acid is also provided herein. The nucleic acid molecule and host cell can be used to generate the antibody.

The antibodies described herein can be used to block homodimerization of VEGFR2 and/or VEGFR3 or heterodimerization of VEGFR2 and VEGFR3, block VEGFR2 and/or VEGFR3 signaling, or block angiogenesis and/or lymphangiogenesis. The antibodies can also be used to detect VEGFR2 and/or VEGFR3 or a fragment thereof in samples in immune assays, e.g., ELISA. The antibodies can bind to, and therefor detect, a fragment of VEFGR2 or VEFGR3 that includes domains IgD6-IgD7.

In addition, the antibodies can be used to treat a solid tumor, e.g., bladder cancer, breast cancer, cervical cancer, colon cancer, rectal cancer, kidney cancer, liver cancer, skin cancer, mesothelioma, lung cancer, oral cancer, ovarian cancer, pancreatic cancer, prostate cancer, sarcoma, and thyroid cancer.

The term "sample" can be any biological sample, e.g., a bodily fluid sample, a blood sample, a cell sample, a urine sample, a saliva sample, or a tissue sample.

Any of the antibodies described herein can be formulated as a pharmaceutical composition suitable for various routes of administration, e.g., intravenous, intraarticular, conjunctival, intracranial, intraperitoneal, intrapleural, intramuscular, intrathecal, or subcutaneous route of administration. The pharmaceutical composition can be an aqueous solution or lyophilized formulation. It can contain a pharmaceutically acceptable carrier, e.g., a buffer, excipient, stabilizer, or preservative. The pharmaceutical composition can include other active ingredients that work together with the antibody, e.g., another therapeutic agent or an adjuvant.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

It was hypothesized that therapeutic antibodies targeting the immunoglobin-like domains 4 to 7 domains of VEGFR-2 would be able to deliver therapeutic benefits independent of ligand concentration and would represent a differentiated mode of action for targeting VEGFR-2 signaling. Described below are the generation of therapeutic antibodies, R2C7-1 and R2C9-11, targeting VEGFR-2 and their inhibitory effects in model systems mimicking angiogenesis and lymphangiogenesis in vitro and in vivo.

Development of a Dual-Functional Antibody to Block VEGF-R2/-R3 Dimerization

Receptor dimerization of VEGFR2 and/or VEGFR3 is a required scenario for activation of their downstream signaling to carry out the biological activities of their specific ligands. Since previous reports have shown that VEGF-A and VEGF-C could cause VEGFR2 homodimerization or heterodimerization with VEGFR3, it was hypothesized that targeting the dimerization region of VEGFR2 might seriously impair the VEGFR2 and/or VEGFR3 receptor-mediated signaling activation resulting in blockade of VEGF-A- and VEGF-C-induced pathogenesis such as angiogenesis, lymphangiogenesis, tumor metastasis, diabetes-associated retinopathy, and vasculitis in rheumatoid arthritis.

To test the hypothesis, a plasmid encoding the dimerization region, immunoglobin-like domains 4 to 7 (IgD4-7), of VEGFR2, was constructed, expressed in the *E. coli* expression system and purified by His-tag affinity columns. After immunization with its recombinant protein, mouse splenocytes were fused with Sp2/0-Ag14 myeloma cells to generate a hybridoma library. Two hybridoma clones (R2C7 and R2C9) were initially chosen for further study based on their high binding affinity to HUVEC cells and a marked capability to inhibit the tube formation. In order to ensure single populations of both clones, two hybridoma cell lines were further selected through a limiting dilution process. The resultant clones were re-named as R2C7-1 and R2C9-11. The functions of both antibodies were further examined, and their physical properties were also characterized in detail.

Dual Targeting of VEGFR2 and VEGFR3

To examine the binding specificity of the newly-developed monoclonal antibodies (mAbs), R2C7-1 and R2C9-11, human umbilical vein endothelial cells (HUVEC) cells and HEK293T cells expressing VEGFR2 (HEK293T/VEGFR) were used as models. Both antibodies had a comparable affinity for VEGFR2 in HUVEC cells (FIGS. 1A and 1C). To further confirm the binding specificity of R2C7-1 and R2C9-11, HEK293T cells were stably-transfected with a plasmid encoding human VEGFR2 or its empty vector (HEK293T/VC). The expression level of VEGFR2 was first determined by a clinical-use VEGFR2 antibody, Ramucirumab. Results obtained from flow cytometric analysis showed that VEGFR2 binding of the newly-developed antibodies was comparable with Ramucirumab. The binding specificity of R2C7-1 and R2C9-11 mAbs was also demonstrated in the HEK293T/VC transfectants, showing trace staining, which was confirmed by a commercial-available antibody against VEGFR2, Abcam9530 (data not shown).

Intriguingly, binding activity of the R2C7-1 and R2C9-11 mAbs was also found in human lymphatic endothelial cells (HLECs) and HEK293T cells expressing VEGFR3. Flow cytometric analysis revealed that the newly-developed mAbs were also able to bind HLECs with a differential affinity (FIG. 1B). Since expression of certain amount of VEGFR2 in HLEC cells has been reported (see, Dellinger et al., 2013, PLoS ONE 8(9): e74686.), HEK293T cells expressing VEGFR3 (HEK293T/VEGFR3) were generated for defining the binding specificity of R2C7-1 and R2C9-11 to VEGFR3. The expression abundance was verified by staining with a commercial-available VEGFR3 antibody, R&D54703 (data not shown). Experiment using flow cytometric analysis clearly demonstrated that, unlike Ramucirumab, both antibodies were capable of binding to VEGFR3 (FIG. 1D). R2C9-11, somehow, showed a higher VEGFR3 binding when compared with the R2C7-1 mAb. Together, data indicated that the newly-developed antibodies had a dual binding capability to VEGFR2 and VEGFR3, suggesting that they might have a dual function of inhibiting angiogenesis and lymphangiogenesis.

Inhibition of Ligand-Induced Receptor Dimerization

Figure 2:
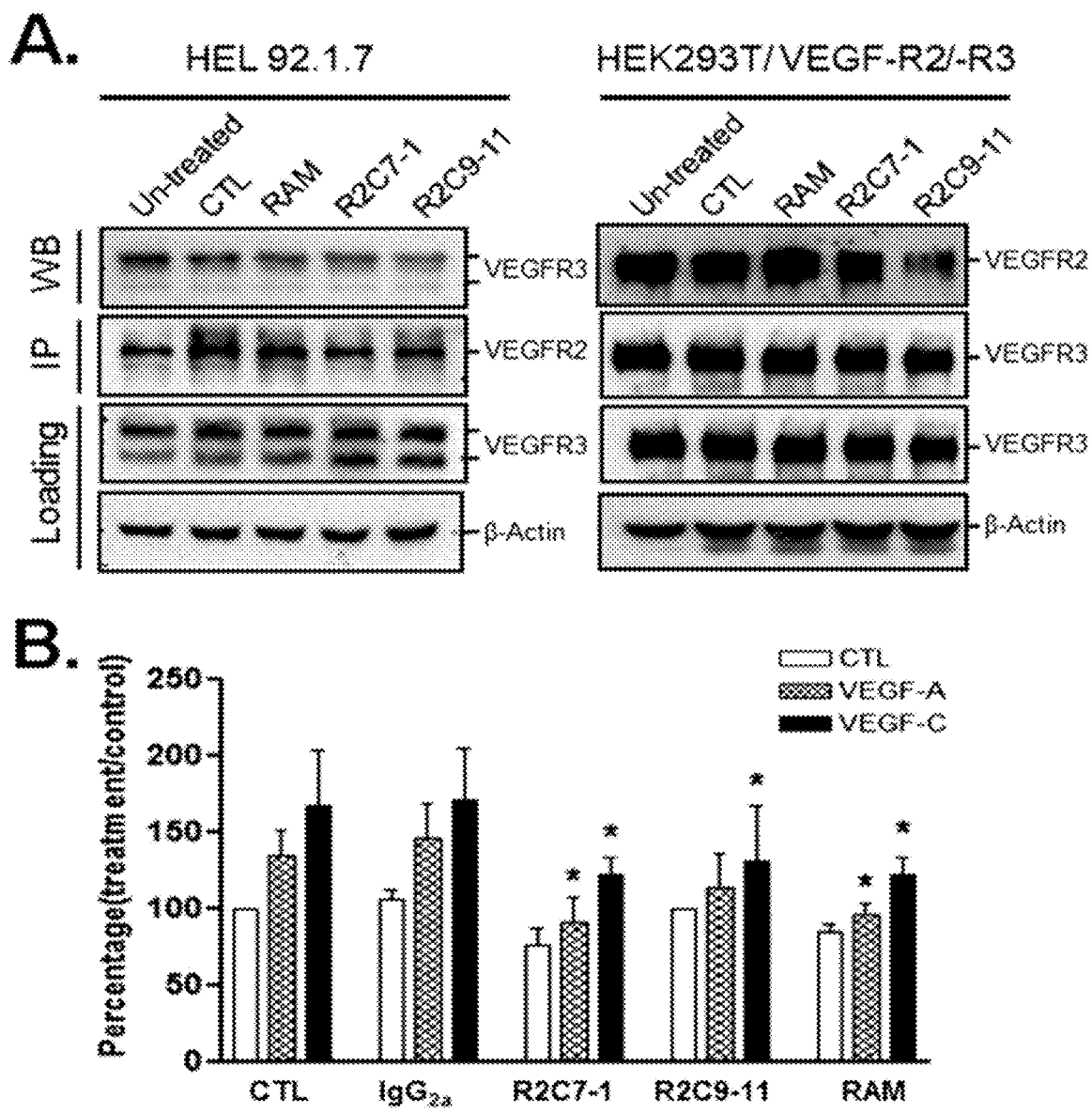
FIG. 2 is a set of blots and graphs showing blockade of the receptor dimerization of VEGFR2 and VEGFR3. Panel A, Co-immunoprecipitation. HEL92.1.7 erythroleukemia cells expressing high-level of VEGFR3 and low-level of VEGFR2 ($1\times10^{10}$/reaction) were untreated or treated with R2C7-1, R2C9-11, or Ramucirumab (20 µg/mL; RAM) at 37° C. for 24 h. IgG2a isotype antibody served as a negative control (CTL). After trysinization and centrifugation, cells were fixed with 1% (w/v) paraformaldehyde, neutralized with glycine solution, and PBS washed. The soluble fraction was obtained by centrifugation, and 25 µg of antibody against VEGFR2 (Abcam9530) were added and incubated at room temperature for 2 h. The antibody-bound protein complexes were immunoprecipitated (IP) by Protein A/G and immune-blotted (WB) for VEGFR3 of HEL92.1.7 cells (left). Total soluble fraction was immuno-probed with antibody specific to VEGFR3 and 13-Actin to show equal loading. Similarly, in order to pulldown VEGFR3 and blot for VEGFR2, HEK293TNEGFR2 cells were transfected with a plasmid encoding for VEGFR3 (right). After 24 h transfection, the transfectants were untreated or treated with R2C7-1, R2C9-11, or Ramucirumab (20 µg/mL; RAM), and immunoprecipitation procedure was performed as described previously. Panel B, Proximity ligation assay (PLA). The inhibitory effect of R2C7-1 and R2C9-11 mAbs (10 µg/mL each) on receptor dimerization of VEGFR2 and/or VEGFR3 was examined by PLA. Cells were seeded and cultured in serum-free media in the presence of R2C7-1, R2C9-11 or Ramucirumab (RAM) for 16 h. Subsequently, cells were stimulated with VEGF-$A_{165}$ or VEGF-C. Each experiment was performed in triplicates, and representative images revealed the close proximity (<40 nm) of VEGFR2 and/or VEGFR3 homo- or hetero-dimerization as demonstrated by the presence of fluorescent products. Nuclei were stained with DAPI. The signals were visualized and quantified by Image J analysis under a fluorescent microscopy with 40× magnification. Results are expressed as mean±S.D. of percentage of cells without antibody treatment (CTL). In addition, cells treated with isotype control (IgG2a) also served as another control. Un-stimulated cells with VEGF-A/-C, with VEGF-A, or with VEGF-C were indicated by blank, double cross, or grey bars, respectively. Statistical significance between cells treated antibody and cells untreated was determined by t-test. "*" represents P<0.05.

To examine whether pretreatment of the R2C7-1 and R2C9-11 mAbs could prevent VEGFR2 and VEGFR3 heterodimerization, HEL92.1.7 expressing high-level VEGFR3 and low-level VEGFR2, and HEK293T co-expressing VEGFR2 and VEGFR3 (HEK293TNEGF-R2/-R3) cells were used as cell models. Experiments using co-immunoprecipitation (IP) assay either to pull down VEGFR2 and blot for VEGFR3 in HEL92.1.7 or pull down VEGFR3 and blot for VEGFR2 in the HEK293TNEGF-R2/-R3 transfectants clearly demonstrated that their inhibitory capability on receptor heterodimerization were superior than that of Ramucirumab, in particular for R2C9-11. See FIG. 2A.

To further investigate whether the newly-developed mAbs had inhibitory effect on VEGF-A- and VEGF-C-induced receptor homo- and/or hetero-dimerization, HLEC cells were used in the proximity ligation assay (PLA). Cells were serum-starved, pre-treated with R2C7-1, R2C9-11, Ramucirumab, or isotype control ($IgG_{2a}$), and followed by stimulation of VEGF-$A_{165}$ or VEGF-C. The formation of homo- and/or hetero-dimerization of VEGFR2 and VEGFR3 were detected when the proximity between the receptors was smaller than 40 nm. Compared to un-stimulated cells (CTL) or $IgG_{2a}$-treated control, results indicated that both R2C7-1 and R2C9-11 mAbs had a comparable inhibitory effect on VEGF-$A_{165}$- and VEGF-C-induced receptor dimerization as compared to that of Ramucirumab. See FIG. 2B. Summarily, although the newly-developed antibodies showed a comparable effect with Ramucirumab on blockade of VEGF-A- and VEGF-C-induced receptor dimerization, they had a better inhibitory effect on heterodimerization than that of Ramucirumab.

Attenuation of VEGFR2 and VEGFR3 Downstream Signaling

After ligand-induced receptor dimerization, initiation of receptor autophosphorylation and its downstream signaling activation is an essential event, accounting for the resultant biological activity of ligand. To investigate whether blockade of receptor dimerization was sufficient to attenuate its downstream signaling, HUVEC cells were starved and pre-treated with R2C7-1 or R2C9-11 mAb or its antibody-isotype control ($IgG_{2a}$). Cells, simultaneously, pre-treated with Ramucirumab served as control. Subsequently, the cells received treatment of VEGF-$A_{165}$, serum stimulation, or no treatment.

Western blot analysis of VEGFR2 auto-phosphorylation and its downstream signaling molecules, such as FAK p38MAPK, demonstrated that inhibition of the receptor dimerization by either newly-developed mAbs or Ramucirumab could significantly attenuate VEGFR2 activation, in particular on tyrosine phosphorylation on the Y1054 residue, even though the inhibitory effect of R2C7-1 was weaker that of Ramucirumab (data not shown).

Intriguingly, different from Ramucirumab-induced p38MARK dephosphorylation, the R2C7-1 mAb did not have any effect on p38MARK activation. Instead, it markedly inactivated FAK activity. As compared to Ramucirumab, R2C9-11 shared the same effect on attenuation of p38MAPK activity (data not shown). For VEGF-A-induced signaling in HLEC cells, both mAbs were shown to have a similar effect on attenuation of VEGFR2 and VEGFR3 auto-phosphorylation (data not shown). In contrast, only R2C9-11 significantly reduced VEGFR3 activity in VEGF-C-induced signaling (data not shown).

Together, although the mechanism underlying blockade of VEGFR2-mediated signaling by the R2C7-1 mAb may be differentially distinct from that of R2C9-11, they both show a dual blockade of VEGFR2 and VEGFR3 receptor-mediated signaling activation.

Blockade of 2-Dimensioned (2D) and 3-Dimensioned (3D) Tube Formation

Figure 3:
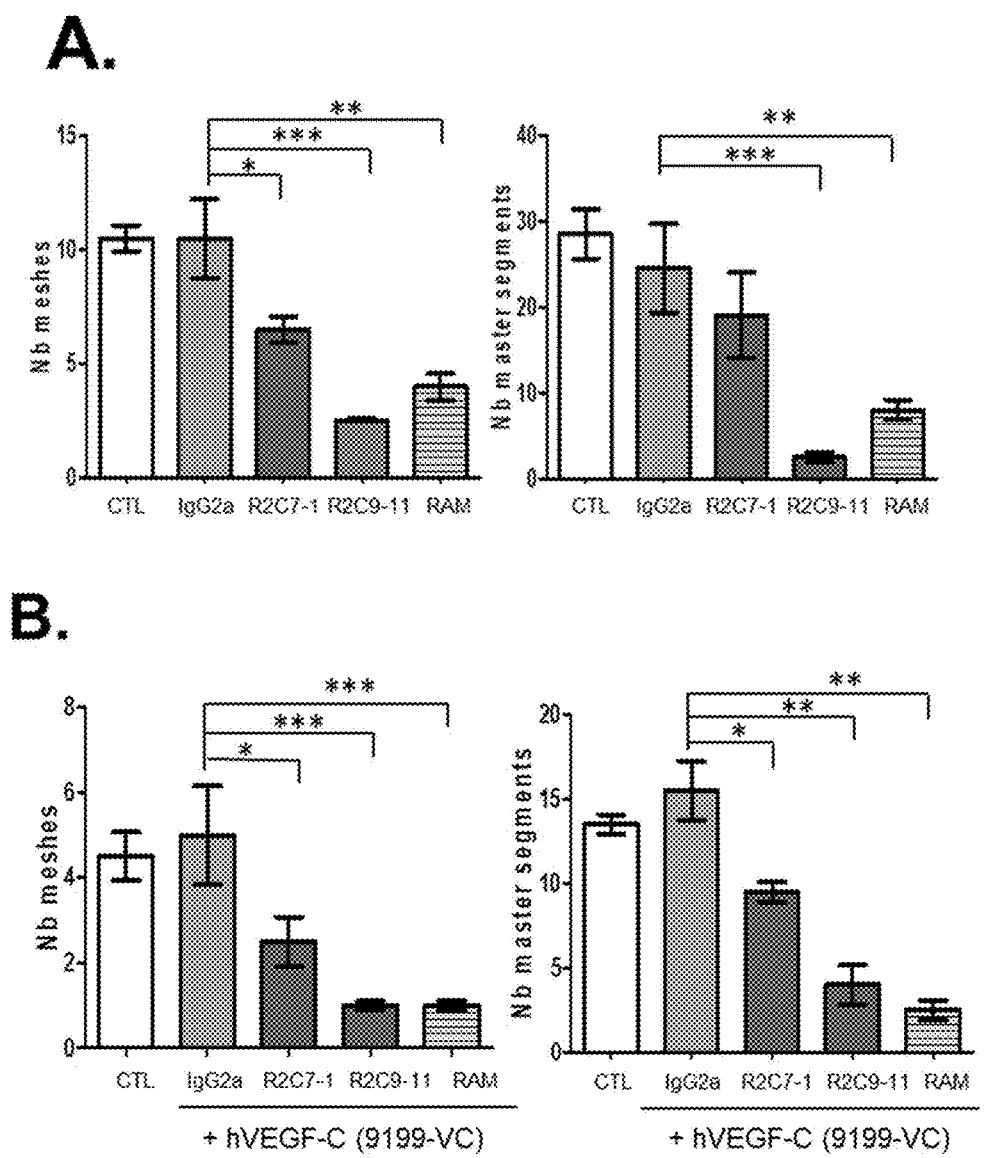
FIG. 3 is a set of graphs showing blockade of human umbilical vein and lymphatic endothelial cell tube formation by VEGFR2 antibodies. HUVEC cells were starved in EGM-2 in the absence VEGFs and other supplements for 8 h. After trysinization, cells were suspended in a medium containing 10 µg/mL of Ramucirumab (RAM), R2C7-1, R2C9-11 or an antibody-isotype control ($IgG_{2a}$), and followed by seeding onto matrigel pre-coated wells. Subsequently, the cells were stimulated with 2 µg/mL VEGF-$A_{165}$ for an additional 10 h at 37° C. Each experiment was performed in triplicates. Panel B, Lymphatic endothelial cells. Similarly, HLEC cells were starved, pre-treated with the above-mentioned antibody and stimulated with 2 µg/mL VEGF-C for 4 h at 37° C. Images were taken and the total number of tube meshes, master junctions, length of tubes, and tubule areas formed were quantified by Angiogenesis Analyzer of Image J. Data are represented as percentages of antibody-isotype control (IgG$_{2a}$) (means±S.D. in triplicate). "*", "", and "*" indicate P<0.05, <0.01, and <0.001, respectively.

To examine whether the attenuation of VEGF-A- and VEGF-C-induced signaling activation by the new-developed antibodies could modulate the biological behavior of HUVEC and HLEC cells, 2D tube formation assay was performed. HUVEC and HLEC cells were seeded onto matrigel-coated wells in the absence of VEGFs and other supplements. The cells were pre-treated with Ramucirumab, R2C7-1, R2C9-11 or an antibody-isotype control ($IgG_{2a}$), and stimulated with VEGF-A or VEGF-C for an additional 10 h. After photography, the total number of tube meshes and master segments were quantified by the angiogenesis analyzer of Image J. The results demonstrated that R2C9-11 had a superior or comparable suppression effect on VEGF-A- or VEGF-C-induced vascular tube formation when compared to those of Ramucirumab. See FIG. 3. However, R2C7-1 mAb was apparently weaker than its counterpart.

Figure 4:
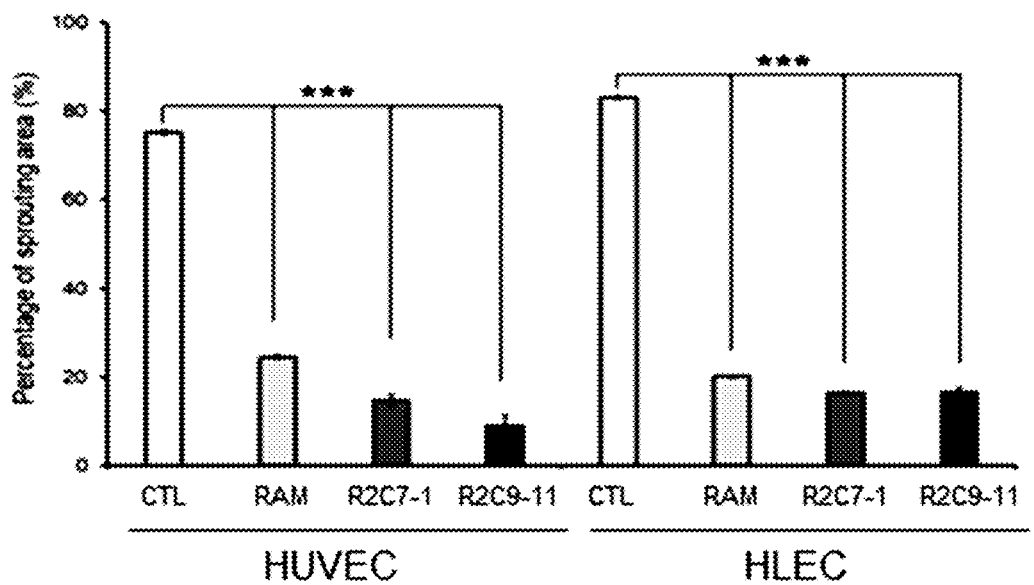
FIG. 4 is a set of graphs showing inhibitory effect of various VEGFR2 antibodies in a 3D angiogenesis model. Endothelial cells (HUVEC and HLEC) were labelled with CFSE and cultured onto ultra-low 96-well plates at 37° C. for 48 h to form cell spheroids. Subsequently, the spheroids were transferred and attached on the matrigel-coated wells by centrifugation and incubation at 37° C. for 30 min. After matrigel embedding, the attached cell spheroids were cultured in medium containing 10 µg/mL of R2C7-1, R2C9-11, Ramucirumab (RAM), or an IgG-isotype control (CTL) antibody, as indicated. The shapes of the core spheroids were observed and photographed under light and fluorescence microscopes. The final images of HUVEC and HLEC were obtained from 7 days after culture, and the fluorescence intensity was analyzed using the NIS-AR software. The area and luminous intensity of the sprouting fibrin were calculated by subtraction of core spheroid from total area and luminous intensity. Data represent mean±S.D. in percentage of control in the sprouting area (Panel A) and in fluorescence intensity (Panel B). The statistical significance between individual VEGFR2 antibody and CTL antibodies was determined by t-test. "***" represents P<0.001.
Figure 4:
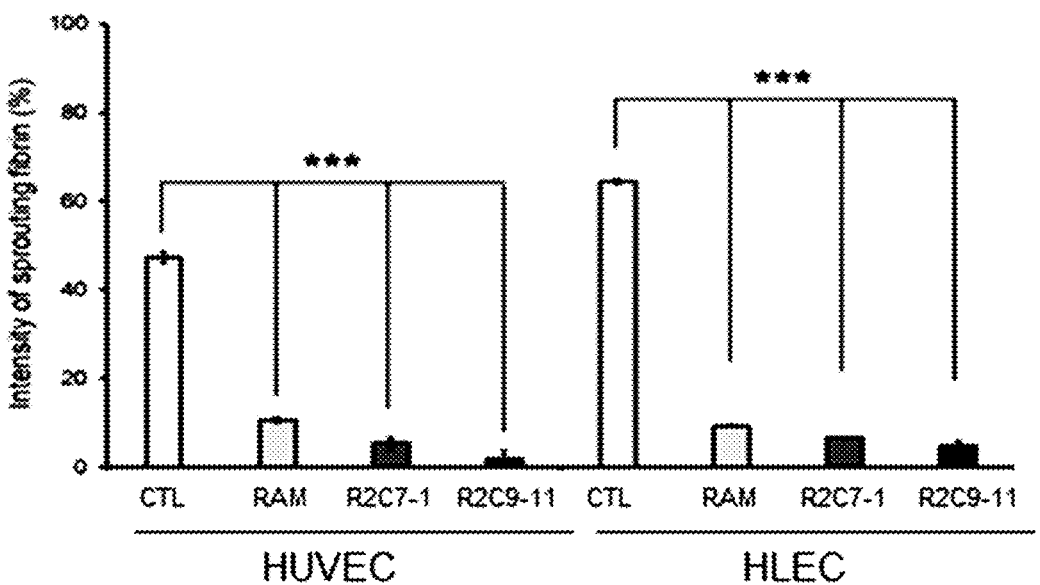

To further examine their suppression function on a different system, 3-dimentioned (3D) sprouting fibrin formation was established by culturing HUVEC and HLEC cells onto ultra-low plates in the presence of CFSE fluorescence tracker to form cell spheroids. After transferring onto precoated matrigel wells, the cells were cultured in medium containing R2C7-1, R2C9-11, Ramucirumab, or isotype control ($IgG_{2a}$) for 7 days. The sprouting area and fluorescence intensity were analyzed with the NIS-AR software. As compared to the sprouting area and fluorescence of control cells, all tested antibodies showed a dramatic capability to suppress sprouting fibrin formation ($P<0.001$). See FIGS. 4A and 4B. Notably, the newly-developed antibodies both displayed a superior suppression effect when compared to that of Ramucirumab. Collectively, R2C7-1 and R2C9-11 mAbs showed a differential capability on inhibition of vascular and lymphatic tube formation depending on the chosen models.

Establishment of Pericyte-Driven Lymphangiogenesis In Vivo

Several reports have demonstrated the pivotal role of pericytes in neovascularization and lymphangiogenesis. See, Ozerdem U, 2006, Ophthalmic Res. 2006; 38(5):251-4. To investigate whether WI38 fibroblasts serving as pericytes could promote lymphangiogenesis in vivo, matrigel plug assay was performed using HLEC cell as a model. HLEC/WI38 mixture was embedded into ice-cold matrigel and subcutaneously inoculated into flanks of NOD-SCID mice. The polymerized matrigels were excised, fixed and embedded into paraffin for 2 or 4 weeks. Immunohistochemical analysis of human WI38 and HLEC cells in the tissue matrigels was performed by double-staining with antibody specific to human α-small muscle actin (SMA) stained with 3,3'-diaminobenzidine (DAB) and CD31 stained with 3-amino-9-ethylcarbazole (AEC), respectively. It was demonstrated that WI38 cells were merged into new vessels in murine tissues, detected with antibody specific to human SMA, before formation of new human lymphatic vessels were found within 2 weeks, which were probed with antibody against human CD31 (data not shown). After 4 weeks, HLEC cells migrated from the right bottom up to left top to form larger lymphatic vessels (data not shown). This data strongly support the important role of pericytes in lymphangiogenesis.

Attenuation of Angiogenesis and Lymphangiogenesis In Vivo

Figure 5:
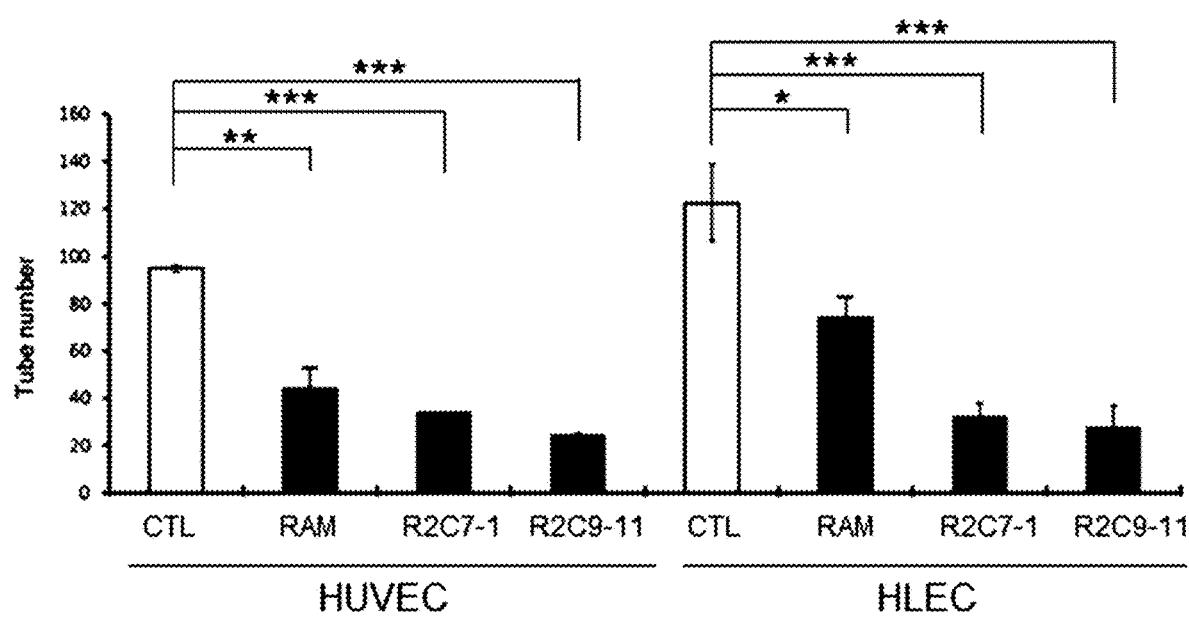
FIG. 5 is a set of graphs showing inhibitory effect of various VEGFR2 antibodies on angiogenesis and lymphangiogenesis in vivo. HUVEC ($1\times10^6$) and HLEC ($1\times10^6$)/WI38 ($2\times10^5$) cell mixtures were suspended in 200 µL ice-cold matrigel and subcutaneously inoculated into the right and left flanks, respectively, of three NOD-SCID mice with an ice-cold syringe with a 24 G-inch needle. The day after inoculation, mice were intravenously injected with R2C7-1, R2C9-11, Ramucirumab (RAM), or an IgG$_{2a}$ control antibody (CTL) (10 mg/kg/mouse) twice per week for 4 weeks. The polymerized matrigels were excised, fixed with 10% formalin overnight, embedded into paraffin and cut into 5 µm-thick tissue sections. Immunohistochemical analysis was performed using a double-staining methodology with antibody specific to human alpha-smooth muscle actin (α-SMA) for WI38 as well as human CD31 for HUVEC and HLEC. The number of AEC-positive tubes was analyzed and quantified using the NIS-AR software. Data are expressed as the mean±S.D. in percentage of control of three independent experiments, and statistical significance between individual VEGFR2 and CTL antibodies was determined by t-test. "*", "", and "*" indicate P<0.05, <0.01, and <0.001, respectively.

Using the same abovementioned model, HUVEC or HLEC cells were pre-mixed with WI38, embedded into matrigels, and subcutaneously inoculated into NOD-SCID mice. Mice were administrated with Ramucirumab, R2C7-1, R2C9-11, or control antibody twice per week for 4 weeks. The tubes partially or fully stained with AEC were quantified using the NIS-AR software. Mice treated with R2C7-lor R2C9-11 displayed a dramatic reduction in vascular vessel formation when compared to control mice, and showed a superior function than Ramucirumab, in particular for lymphangiogenesis. See FIG. 5.

Figure 6:
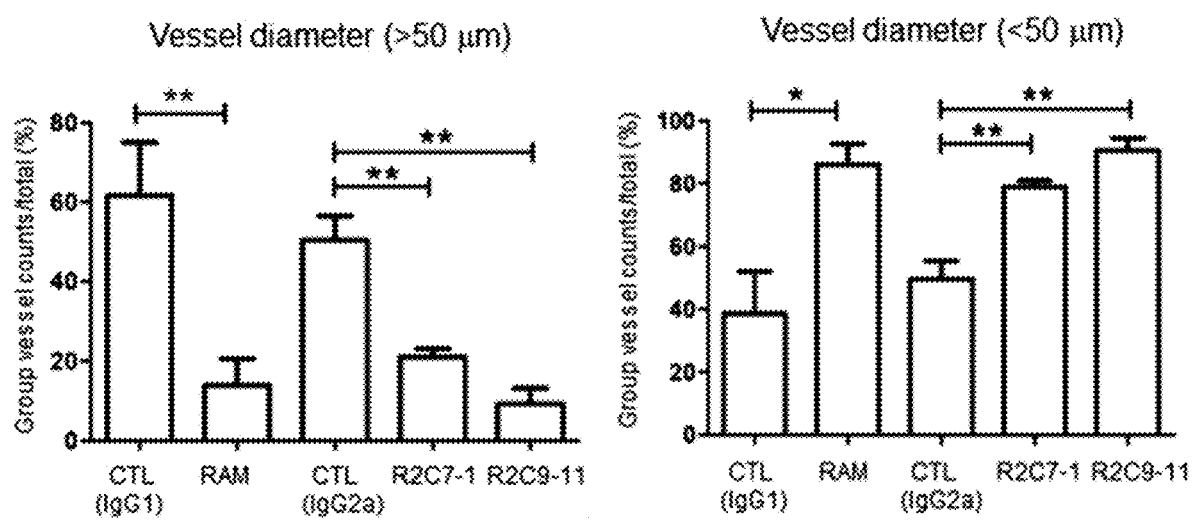
FIG. 6 is a set of graphs showing determination of the ratio of large and small vessel after treatment of VEGFR2 antibody. The Matrigel/HUVEC cells mix ($1\times10^6$ cells/500 µL matrigel plug) was subcutaneously inoculated into the abdominal midline of NOD SCID mice. The antibodies (IgG$_1$ CTL, Ramucirumab (RAM), IgG$_{2a}$ CTL, R2C7-1 or R2C9-11) were intraperitoneally injected into the mice (10 mg/kg) at Day 7, 14, 21 and 28 after matrigel plug implantation. The mice were sacrificed at Day 35. The tissue gel plugs were fixed with 10% formalin for 24 h, embedded in paraffin, and cut into 5-µm-thick sections. The tube formation of HUVEC cells was distinguished by immunohistochemically staining with anti-human CD31 (hCD31) antibody to analyze the suppressive effect of the antibodies on angiogenesis in vivo. The diameter of the hCD31-positive blood vessels was determined by microscopy, sorted into two groups, either > or <50 µm in diameter, and the number of vessels in each group was quantified. The ratio of number of vessel (>50 µm)/total vessel in each antibody treatment is shown in the left panel. The ratio of number of vessel (<50 µm)/total vessel is shown in the right panel. Data are represented as mean±S.D. of two independent experiments. Statistical significance between individual VEGFR2 and their corresponding CTL antibodies was determined by t-test. "*" and "**" indicate P<0.05 and P<0.01, respectively.

In addition, the ratio of vessels in size was also determined. It was shown that that the ratio of vessels with size larger than 50 μm diameter was significantly decreased; in contrast, the ratio of vessel size smaller than 50 μm diameter was markedly increased when mice were administrated with R2C7-1, R2C9-11, or Ramucirumab. See FIG. 6. The phenomenon was also observed in lymphatic vessel formation using HLEC as a model, consistently demonstrating that R2C7-1 and R2C9-11 had a superior effect on inhibition of lymphatic vessel formation as compared to Ramucirumab (data not shown). Thus, the data showed that dual targeting of VEGFR2 and VEGFR3 by the newly-developed antibodies may provide a better inhibition effect on angiogenesis and lymphangiogenesis than Ramucirumab.

Antibody-Dependent Tumor Cytotoxicity In Vitro and In Vivo

Figure 7:
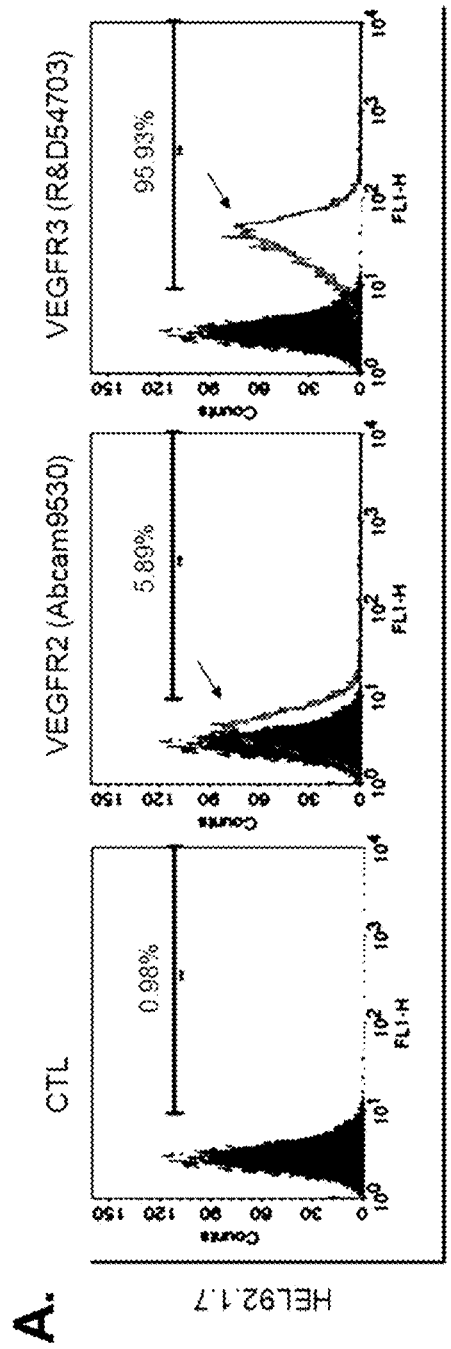
FIG. 7 is a set of graphs showing antibody-dependent cytotoxicity of various VEGFR2 antibodies. Panel A, expression profile of VEGFR2 and VEGFR3. HEL92.1.7 cells were stained with antibody against VEGFR2 (Abcam9530) or VEGFR3 (R&D54703), as indicated with arrow. The percentage of expression levels of those receptors was determined when compared to cells stained with antibody isotype control (CTL). Panel B, antibody-dependent cytotoxicity (ADCC). HEL92.1.7 cells ($5\times10^4$/well in 25 µL) were seeded onto 96-well while plates, followed by addition of designed concentrations of R2C7-1, R2C9-11, or Ramucirumab (25 µL/each; RAM), and further incubation at 37° C. for 15 min. Peripheral blood mononuclear cells (PBMC) were prepared from NOD-SCID mice using the PBMC isolation kit (MyBioSource) and suspended in RPMI1640 medium containing 4% baby rabbit serum at a concentration of $4.0\times10^6$ cells/mL. Fifty µL of PBMC effectors were mixed with each well of HEL92.1.7 target cells at the ratio of 4 to 1. After addition of PrestoBlue™, the cell mixtures were incubated at 37° C. for 20 h. The cell viability was determined by the fluorescence intensity (560 nm/590 nm).
Figure 7:
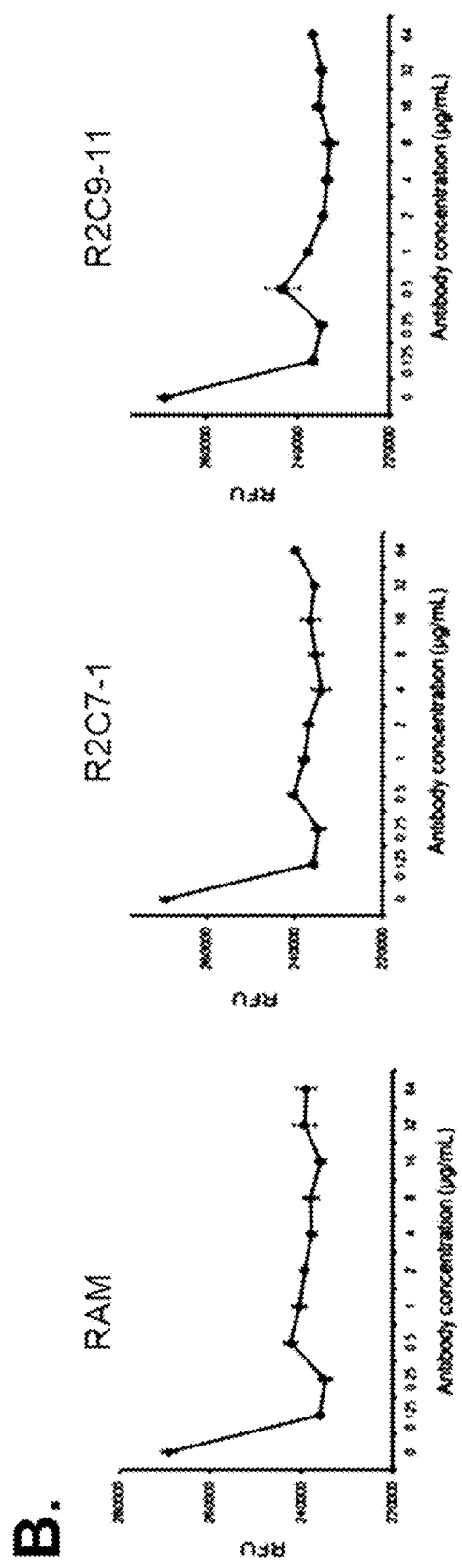

Since the newly-developed antibodies could specifically target VEGFR3, their cytotoxic capability was closely examined in cells expressing VEGFR3. HEL92.1.7 cells were used, and the expression status of VEGFR2 and VEGFR3 was first characterized. Flow cytomeric analysis of HEL92.1.7 clearly revealed its high expression of VEGFR3 (~95%), but low expression of VEGFR2 (~5%). See FIG. 7A. Experiments using peripheral blood mononuclear cells (PBMCs) isolated from NOD-SCID mice to conduct antibody-dependent cytotoxicity (ADCC) showed that all tested antibodies, including Ramucirumab, displayed a remarkable ability to kill HEL92.1.7 tumor cells in the presence of PBMCs and 2% baby serum, even at a low concentration of 0.125 g/mL of antibody. See FIG. 7B.

Figure 8:
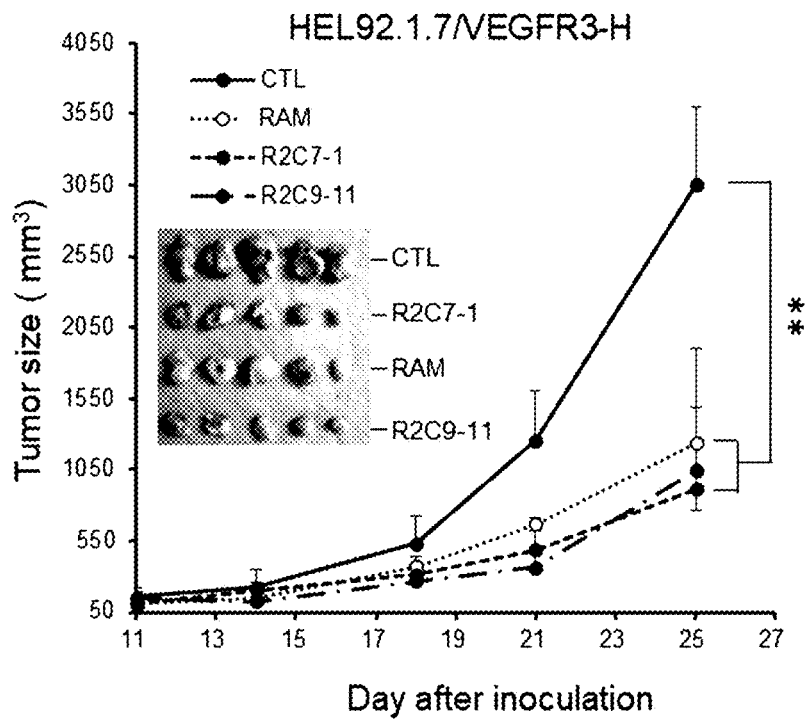
FIG. 8 is a set of graphs showing suppression of tumor growth by individual VEGFR2 antibodies. HEL92.1.7 cells with higher expression level of VEGFR3 (>95% of the population; VEGFR3-H in Panel A) were separated from cells with lower expression (<5% of the population; VEGFR3-L in Panel B) using cell sorter flow cytometry (Beckman Coulter CytoFLEX S), and followed by cell expansion. High-expressing and low-expressing cells ($1\times10^6$/mouse) were subcutaneously injected into the right and left sides, respectively, of the dorsal flanks of the same mouse. Seven days after tumor inoculation, 5 mice/group received the designated antibody treatments (Ramucirumab (RAM), R2C7-1 or R2C9-11) at a dose of 5 mg/kg/mouse, twice per week for 25 days after Day 7. Mice administrated with the IgG$_{2a}$-isotype control (CTL) were treated in the same manner. The tumor volume of the individual mice was measured twice per week. The differences between individual antibody treatments and the control in the averages of the tumor sizes (insets in Panel A and Panel B) were statistically determined by t-test analyses after mice killing. "*" and "**" indicate P<0.05 and P<0.01, respectively.
Figure 8:
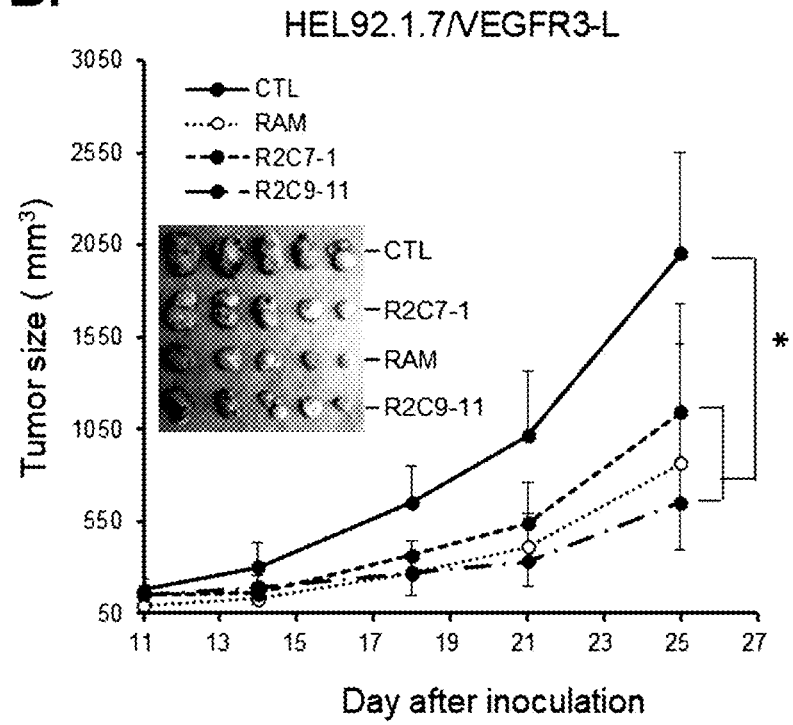

The tumor suppression effect of these antibodies was further investigated in xenografted tumor in NOD-SCID mice. Cells expressing high- (~95%) or low-level (~5%) VEGFR3 were sorted and expanded. Cells with high or low level of VEGFR3 were inoculated into the right or left flanks of mice. Seven days after tumor inoculation, mice were administered with R2C7-1, R2C9-11, Ramucirumab or an IgG control antibody twice per week for 25 days. It was demonstrated that the newly-developed antibodies had a comparable therapeutic effect with Ramucirumab for tumors expressing either high or low level of VEGFR3. See FIG. 8. Summarily, besides dual function on inhibition of blood and lymphatic vessel formation, R2C7-1 and R2C9-11 could trigger ADCC killing effect and suppress growth of tumor cells expressing VEGFR3. The suppression potency was highly comparable to Ramucirumab in a 25-day therapy.

Combined Therapy of the Newly-Developed Antibody with Ramucirumab

Figure 9:
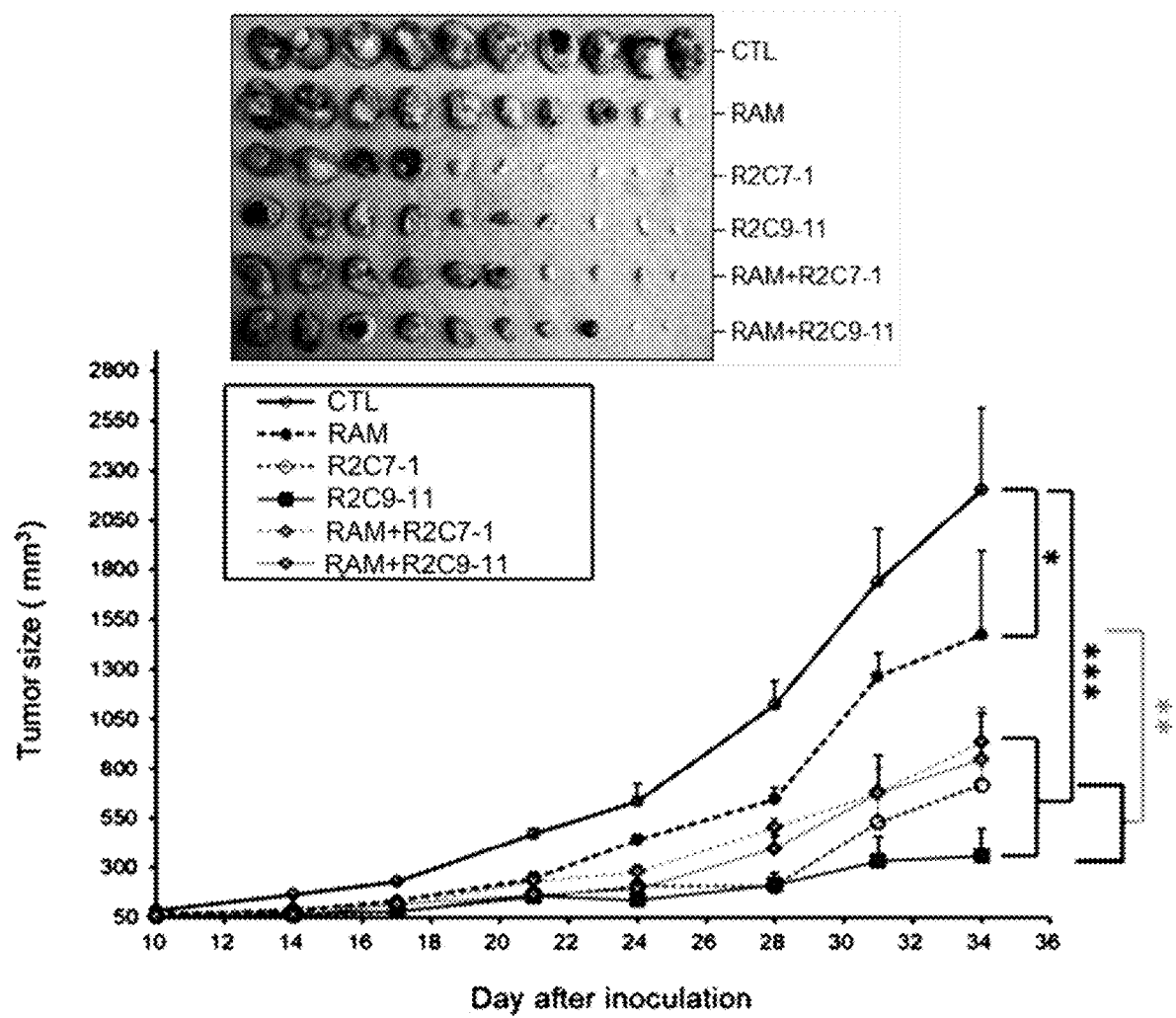
FIG. 9 is a graph showing the inhibitory effect of combined VEGFR2 monoclonal antibodies on tumor growth. HEL92.3.1 cells ($1\times10^6$/mouse) were subcutaneously inoculated into NOD-SCID mice. Ten mice/group and total 6 groups were treated with R2C7-1, R2C9-11, or their combination with Ramucirumab (RAM), as indicated. Seven day after tumor inoculation, mice were intravenously administrated with R2C7-1, R2C9-11, Ramucirumab alone (5 mg/kg/mouse) or a combination of Ramucirumab (5 mg/kg) with R2C7-1 or R2C9-11 (5 mg/kg) twice a week for 35 days. The IgG$_{2a}$-isotype control (CTL) antibody was used to bring the total amount of antibody up to 10 mg/kg in each mouse treated with R2C7-1, R2C9-11, or Ramucirumab alone. The tumor volume of individual mice was measured according to the modified ellipsoidal formula [tumor volume=½(length×width²)] (Tomayko M M, Reynolds C P., 1989). Data are represented as mean±S.D. of the averages of the tumor sizes (inset), and statistical significance between VEGFR2 and CTL antibodies was determined by t-test. "*", "", and "*" represent P<0.05, <0.01, and <0.001, respectively.

To investigate whether combination of the newly-developed antibody with Ramucirumab could provide a better benefit for tumor suppression, mice (10 mice/group) receiving R2C7-1, R2C9-11, or Ramucirumab alone or combined were examined using HEL92.1.7 as a model. Intravenous administration of the antibodies (total 10 mg/kg) was performed 7 days after inoculation, twice per week for 35 days. Intriguingly, combination of R2C7-1 or R2C9-11 with Ramucirumab did not bestow a better therapy on tumor suppression when compared to the R2C7-1 or R2C9-11 treatment alone. However, the R2C9-11 treatment alone could significantly provide a superior therapy effect than other antibodies or combination. See FIG. 9. Thus, the data strongly suggest that targeting VEGFR3-expressing tumor cells like HEL92.1.7 may not only attenuate their cell survival, but also induce tumor cytotoxicity by targeting with tested antibodies in the presence of activated complements in baby serum.

Recognition Epitope of the Newly-Developed Antibodies

Figure 10:
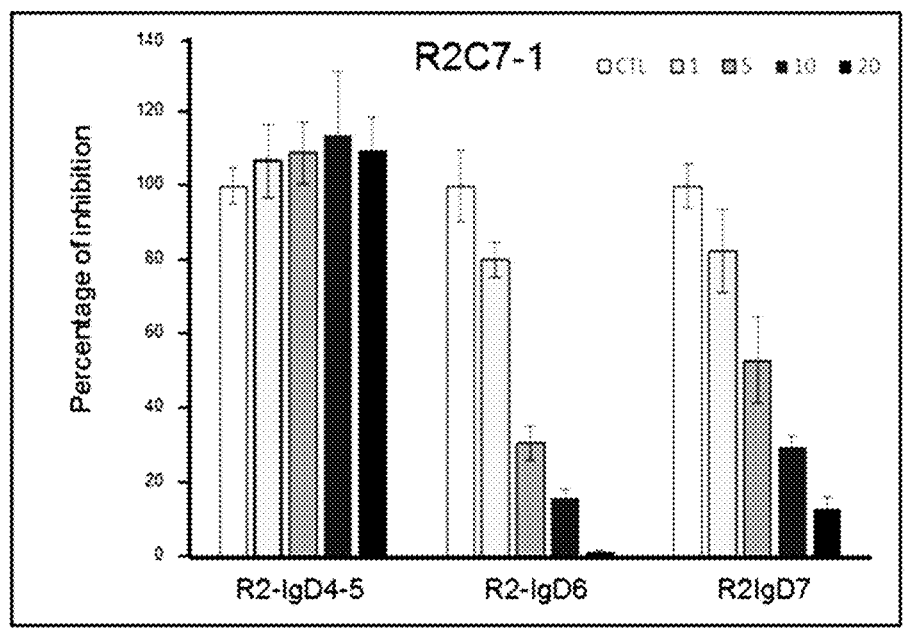
FIG. 10 is a set of graphs showing characterization of the binding epitopes of R2C7-1 and R2C9-11 antibodies on VEGFR2. HEK293T expressing VEGFR2 (293T/VEGFR2) were seeded on 96-well plates at a density of 5×10⁴ cells/100 µL/well and incubated overnight at 37° C. After 293T/VEGFR2 cells were fixed with glutaraldehyde and washed, the optimal concentrations of R2C7-1 and R2C9-11 antibodies for binding to the cells were determined using a standard ELISA procedure. The optimal concentration of R2C7-1 and R2C9-11 mAbs (200 µg/mL and 50 µg/mL, respectively) were absorbed with the designated doses of the individual immunoglobin-like domains of VEGFR2 (R2-IgDs) antigens. After, the fixed 293T/VEGFR2 cells were incubated with the absorbed antibodies at 37° C. for 30 min. The bound antibodies were probed with goat-anti-mouse IgG conjugated with HRP, visualized by addition of ABTS, and measured at $OD_{405}$ using the SpectraMax microplate reader. Data are represented as means±S.D. of the percentage of isotype control (CTL) in triplicate. The potential epitope locations of R2C7-1 (upper) and R2C9-11 (lower) on the VEGFR2 antigen are indicated by black lines spanning IgD6 and IgD7 in the schematics.
Figure 10:
Figure 10:
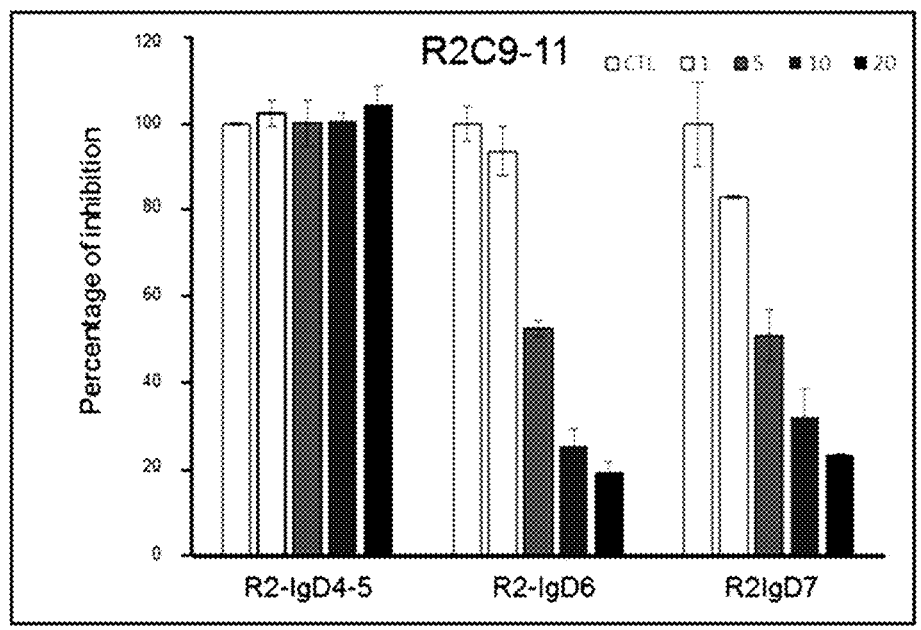
Figure 10:

To define the recognition epitopes of R2C7-1 and R2C9-11 antibodies, cell-based competitive enzyme-linked immunosorbent assay (ELISA) was performed. HEK293TNEGFR2 transfectants ($5\times10^4$/well) were coated and fixed on 96-well plates. The optimal concentrations, the highest concentration of the log phase, of R2C7-1 and R2C9-11 antibodies for binding to the cells, were determined using a standard ELISA procedure (data not shown). Subsequently, the antibodies with the optimal concentrations were absorbed with designed doses of individual recombinant extracellular domains of VEGFR2 (R2-IgDs) for competing the binding epitopes. It was determined that the major recognition epitopes of both R2C7-1 and R2C9-11 were located in between IgD6 and IgD7, but showed a slight difference. R2C7-1 displayed a stronger binding to IgD6 when compared to R2C9-11. See FIG. 10. To further define the epitopes of the newly-developed antibodies, alanine scanning mutagenesis was carried out. Any amino-acid change between IgD6 and IgD7 of VEGFR2 caused a dramatic loss of the binding capability of both antibodies (data not shown), indicating that the recognition epitopes of the newly-developed antibodies could be structural epitopes.

Figure 11:
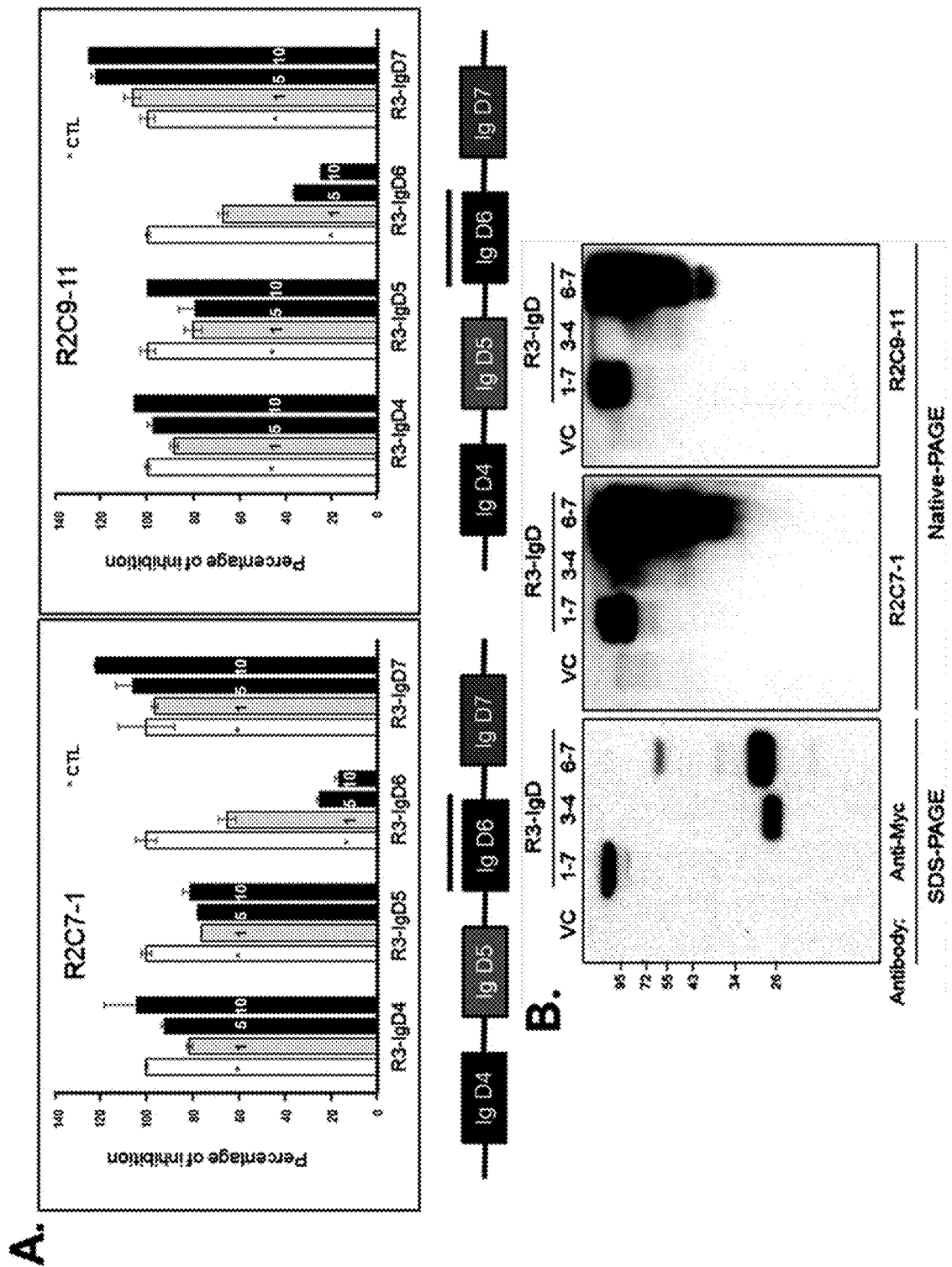
FIG. 11 is a set of graphs showing determination of the binding epitopes of R2C7-1 and R2C9-11 antibodies on VEGFR3 antigen. Panel A, Cell-based competitive. ELISA. HEK293T cells expressing VEGFR3 (293T/VEGFR3) were coated in 96-well plates. The optimal concentrations of R2C7-1 and R2C9-11 mAbs were determined as described previously (data now shown). The optimal concentrations of R2C7-1 and R2C9-11 mAbs were absorbed with the designed doses of the individual immunoglobin-like domains of VEGFR3 (R3-IgDs) antigens, as indicated. The bound antibodies were immune-probed with secondary antibody conjugated with HRP, visualized by addition of ABTS, and measured at $OD_{405}$ using a microplate reader (SpectraMax). Data are represented as means±S.D. of percentage of isotype control (CTL) in triplicate. The epitope locations of R2C7-1 and R2C9-11 on the VEGFR3 antigen are indicated by the black lines spanning IgD6 in the schematics. Panel B, Native gel electrophoresis. The whole extracellular domain (R3-IgD1-7), domain 3-4 (R3-IgD3-4) and domain 6-7 (R3-IgD6-7) were constructed, expressed in the *E. coli*, and purified using the anti-Myc affinity purification system. The purity and molecular weight of each recombinant protein were visualized with a standard Western blot using anti-Myc antibody as probe (left). The binding of R2C7-1 and R2C9-11 to the VEGFR3 truncated antigens was evaluated with native gel electrophoresis to confirm the epitopes of R2C7-1 and R2C9-11 mAbs (middle and right, respectively).

The same methodology was adopted to define the epitopes of the antibodies on VEGFR3. To determine the optimal concentrations of the antibodies for VEGFR3, HEK293T/VEGFR3 transfectants were used as targets (data not shown). Subsequently, the antibodies with optimal concentrations were absorbed with individual recombinant extracellular domains of VEGFR3 (R3-IgDs) for competing the binding epitopes. Similarly, their major epitopes were both located in IgD6, but not in IgD7, of VEGFR3. See FIG. 11A. To conform this finding, Western blotting analysis of different recombinant IgD proteins was carried out using native gel electrophoresis. Since IgD5 was reported to undergo proteolytic cleavage after VEGFR3 receptor biosynthesis (see Pajusola K et al., 1994, Oncogene. 9(12):3545-55) and it also showed no competitive capability in the cell-based ELISA (see FIG. 11A), IgD1-7, IgD3-4, and IgD6-7 fragments were expressed and generated in the *E. coli* system. After non-reduced gel electrophoresis, the purified proteins were immuno-probed with R2C7-1 and R2C9-11 antibodies, showing they had a remarkably high ability to bind to IgD6-7, but not IgD3-4 (FIG. 11 B). Together, the data strongly indicated that the epitopes of R2C7-1 and R2C9-11 for VEGFR2 and VEGFR3 were both located in IgD6-7, and the recognition sites on VEGFR3 protein was specifically located in the IgD6.

Complementarity-Determining Regions (CDRs) and Binding Affinity

To define CDRs of the antibodies, the Kabat and Chothia systems were applied to define the variable regions of R2C7-1 and R2C9-11 antibodies. In order to confirm that both antibody-secreting hybridomas were single clone, the cells were selected by two consecutive serial dilutions. The genes encoding the antibodies were cloned out by RT-PCR using 5'-RACE or 5'-/3'-degenerated IgG-specific primers. See Table 1. The CDRs cloned out from the newly-developed antibodies are shown in Table 2. The amino-acid sequences of the heavy chain CDR1 (CDR-H1) and CDR2 (CDR-H2) defined by the Kabat and Chothia systems were shown to be greatly different in R2C7-1 and R2C9-11, but there was no distinction in the heavy chain CDR3 (CDR-H3). For defining CDR regions of the light chains, the two systems displayed no difference. Taken the data together, because of variations in the amino-acid sequences of the CDRs between R2C7-1 and R2C9-11, these two antibodies may have distinct binding epitopes on the VEGFR2 and VEGFR3, although both showed potential binding on the IgD6-7 domains.

TABLE 1

Sequences of the VEGFR2 mAbs

| R2C7-1 | (SEQ ID NO: 1) |
|---|---|
| $V_H$ | EVQLQQSGPELVKPGASVKISCKASGYSFTDYFINWVIQRH GKSLEWVGRINPYNGGSFYNQKFKDKATLTVDKSSNIAHME LRSLASEDSAIYYCARSGGNGYDYWGQGTTLTVSS |
| R2C7-1 | (SEQ ID NO: 2) |
| $V_L$ | DIVMTQAAPSVPVIPGESVSISCRSSKSLLHSNGNTYLYWF LQRPGQSPQLLIYRMSNLASGVPDRFSGSGSGTAFTLRISR VEAEDVGVYYCMQHLEYPYFGGGTKVEIK |
| R2C9-11 | (SEQ ID NO: 3) |
| $V_H$ | QVQLQQPGAELVKPGASVKLSCKASGYTFTSYWMHWVKQRP GQGLEWIGEINPSNGRTNYNEKFKSKATLTVDKSSSTAYMQ LSSLTSEDSAVYYCANLYFDVWGAGTTVTVSS |
| R2C9-11 | (SEQ ID NO: 4) |
| $V_L$ | DIVMTQSPSSLSVSAGEKVTMSCKSSQNLLNSGNQKYYLAW YQQKPGQPPKLLIYGASIRESGVPDRFIGSGSGTDFTLTIS SVQAEDLAVYFCQSDHSYPYTFGGGTKLEIK |

TABLE 2

Complementarity-determining regions (CDRs) of the VEGFR2 mAbs

| Antibody | CDR-1 | CDR-2 | CDR3 |
|---|---|---|---|
| R2C7-1; $V_H$-Kabat | DYFIN (SEQ ID NO: 5) | RINPYNGGSFYNQKFKD (SEQ ID NO: 6) | SGGNGYDY (SEQ ID NO: 7) |
| R2C7-1; $V_H$-Chothia | GYSFTDY (SEQ ID NO: 8) | NPYNGG (SEQ ID NO: 9) | SGGNGYDY (SEQ ID NO: 7) |
| R2C7-1; $V_L$-Kabat | RSSKSLLHSNGNTYLY (SEQ ID NO: 10) | RMSNLAS (SEQ ID NO: 11) | MQHLEYPYT (SEQ ID NO: 12) |
| R2C7-1; $V_L$-Chothia | RSSKSLLHSNGNTYLY (SEQ ID NO: 10) | RMSNLAS (SEQ ID NO: 11) | MQHLEYPYT (SEQ ID NO: 12) |
| R2C9-11; $V_H$-Kabat | SYWMH (SEQ ID NO: 13) | EINPSNGRTNYNEKFKS (SEQ ID NO: 14) | LYFDV (SEQ ID NO: 15) |
| R2C9-11; $V_H$-Chothia | GYTFTSY (SEQ ID NO: 16) | NPSNGR (SEQ ID NO: 17) | LYFDV (SEQ ID NO: 15) |
| R2C9-11; $V_L$-Kabat | KSSQNLLNSGNQKYYLA (SEQ ID NO: 18) | GASIRES (SEQ ID NO: 19) | QSDHSYPYT (SEQ ID NO: 20) |
| R2C9-11 $V_L$-Chothia | KSSQNLLNSGNQKYYLA (SEQ ID NO: 18) | GASIRES (SEQ ID NO: 19) | QSDHSYPYT (SEQ ID NO: 20) |

Note:
the Complementarity-determining regions of the antibodies were defined by either the Kabat or Chothia numbering schemes, as indicated.

TABLE 3

Determination of binding affinity of R2C7-1 and R2C9-11 by Biacore.

| Flow Analyte | Ligand | Ka (1/ms) | Kd (1/s) | KD (nM) | Chi$^2$ | Flow Analyte | Ligand | Ka (1/Ms) | Kd (1/s) | KD (nM) | Chi$^2$ |
|---|---|---|---|---|---|---|---|---|---|---|---|
| | | Ligand: VEGFR2 (KDR)-IgD 4-7 | | | | | | Ligand: VEGFR3 (Flt-4)-IgD 4-7 | | | |
| R2C7-1 | KDR-IgD4-7 | $1.10 \times 10^6$ | $2.40 \times 10^{-3}$ | $2.18 \times 10^{-9}$ | $1.90 \times 10^3$ | R2C7-1 | Flt 4-IgD4-7 | $1.50 \times 10^6$ | $4.90 \times 10^{-3}$ | $3.30 \times 10^{-9}$ | $1.90 \times 10^3$ |
| R2C9-11 | KDR-IgD4-7 | $2.9 \times 10^4$ | $1.30 \times 10^{-5}$ | $4.60 \times 10^{-10}$ | $6.30 \times 10^3$ | R2C9-11 | Flt 4-IgD4-7 | $3.20 \times 10^6$ | $3.40 \times 10^{-3}$ | $1.10 \times 10^{-9}$ | $6.20 \times 10^3$ |
| | | Ligand: VEGFR2 (KDR)-IgD 6-7 | | | | | | Ligand: VEGFR3 (Flt-4)-IgD 6-7 | | | |
| R2c7-1 | KDR-IgD6-7 | $9.70 \times 10^3$ | $1.10 \times 10^{-5}$ | $1.13 \times 10^{-9}$ | $1.30 \times 10^3$ | R2C7-1 | Flt 4-IgD6-7 | $2.80 \times 10^5$ | $3.70 \times 10^{-3}$ | $1.30 \times 10^{-8}$ | $3.10 \times 10^3$ |
| R2C9-11 | KDR-IgD6-7 | $6.60 \times 10^2$ | $1.00 \times 10^{-6}$ | $1.50 \times 10^{-9}$ | $4.80 \times 10^{-3}$ | R2C9-11 | Flt 4-IgD6-7 | $7.90 \times 10^6$ | $3.80 \times 10^{-2}$ | $4.80 \times 10^{-9}$ | $3.10 \times 10^3$ |

To determine the binding affinity of R2C7-1 and R2C9-11, recombinant IgD4-7 and IgD6-7 of VEGFR2 (KDR218384) and VEGFR3 (Flt-4) were used as target antigens, and binding affinity was measured by a Biacore system. Results in Table 3 consistently demonstrated that R2C9-11 had a higher affinity for the IgD4-7 and IgD6-7 antigens of VEGFR2 and VEGFR3 than R2C7-1. Binding to VEGFR2 by either antibody was stronger than binding to VEGFR3. In addition, binding to IgD4-7 of VEGFR2 or VEGFR3 by both of the newly-developed antibodies was slightly higher than their binding to IgD6-7. These data also suggested that the recognition epitopes of R2C7-1 and R2C9-11 depend on the 3-dimentional structures of the extracellular domains of VEGFR2 and VEGFR3.

Materials and Methods (1) Cell Culture

NHK293T cells were cultured in DMEM supplemented by 10% FBS and 1× Antibiotic-Antimycotic (GIBCO; Grand Island, N.Y.) at 37° C. in 5% $CO_2$ incubator. Human umbilical vein endothelial cells (HUVEC) cells were maintained in endothelial basal medium-2 (EGM-2) plus a variety of growth factors, cytokines and other supplements in the SingleQuot kit (Lonza; Basel, Switzerland) at 37° C. in 5% $CO_2$ incubator. The primary cells used in experiments were around $3^{rd}$_$6^{th}$ passages. Human lymphatic endothelial cells (LECs) were purchased from Promocell (Heidelberg Germany) and cultured in endothelial cell medium MV (Promocell), according to the manufacturer's instructions.

(2) Generation of Hybridomas

A BALB/C mouse was intraperitoneally (IP) immunized with the human recombinant immunoglobin (Ig) domains 4-7 of vascular endothelial growth factor receptor 2 (VEGFR2) three times at two-week intervals. Gene encoding extracellular domains 4-7 of VEGFR2 was generated by PCR using gene-specific primers and the first-strain cDNA library of HUVEC as template, and subsequently cloned into the pGEX-KG vector. The resultant plasmid, pGEX-VEGFR2-ED Ig D4-7, was verified by direct sequencing. The encoded protein was expressed in the E. coli expression system and purified using glutathione-conjugated Sepharose beads (Sigma-Aldrich; St. Louis, Mo.), as described in the following "Gene construct and expression" section. Sera were collected and tested for the presence of anti-VEGFR2 antibody by indirect enzyme-linked immunosorbent assay (ELISA). After a high level of antibody titer (>1:3000 dilution) was detected, the mouse received a final IP boost with 25 µg of the recombinant antigen in the absence of Freund's adjuvant. Five days after the last boosting, the mouse was sacrificed. Its spleen cells were collected and fused with myeloma cells by a modified hybridoma technique (see, Apiratmateekul, N., P. Phunpae, and W. Kasinrerk, Cytotechnology, 2009. 60(1-3): p. 53.). In brief, the splenocytes ($7 \times 10^7$ cells) were fused with $2 \times 10^7$ Sp2/0-Ag14 (ATCC CRL-1581™) cells using 50% polyethylene glycol 4000 (PEG 4000; Sigma-Aldrich, St. Louis, Mo.) by a standard hybridoma technique. After HAT medium (Sigma-Aldrich) selection, the culture supernatants obtained from the hybridoma-containing wells were analyzed for antibody-antigen reactivity using a standard indirect ELISA procedure. Hybridomas with values of optical density at 450 nm ($013_{450}$ nm) ≥0.60 were considered as positive, and single cell cloning of the positive wells was performed using the limiting dilution technique. The isotypes of the secreted murine monoclonal antibodies (mAbs) was determined using a murine mAb isotyping kit (Thermo Scientific Pierce, Rockford, Ill.).

(3) Antibody Purification

Hybridomas producing anti-VEGFR2 mAbs were cultured in serum-free condition using a hybridoma serum-free medium (Gibco). The mAbs were purified from culture supernatants by affinity chromatography using TOYOPE-ARL AF-rProtein A (Griesheim, Germany). After washing with ice-cold PBS (10× bed volume), antibody captured by protein A beads was eluted with Elution buffer (50 mM glycine-HCl, pH 3.0 for R2C7-1 or 50 mM glycine-HCl/150 mM NaCl, pH 3.0 for R2C9-11). The eluted fraction was collected in tube containing 100 µL Neutralization buffer (1 M Tris-HCl, pH 8.0/1.5 M NaCl/1 mM EDTA; 1 mL/tube). The purity and activity by sodium dodecyl sulfate polyacrylamide gel electrophoresis (SDS-PAGE) and indirect ELISA, respectively. The concentration of mAb was determined using Bradford protein assay (Bio-Rad, Hercules, Calif.) and dialyzed against PBS at 4° C. overnight. After that, the anti-VEGFR2 Ab was stored at −80° C. for further use.

(4) Tube Formation Assay

Culture wells were coated with ice-cold matrigel (80 µL/well; BD Biosciences, San Jose, Calif.) and followed by incubating at 37° C. for 30 min for gel formation. LECs and HUVECs were starved in the EGM-2 in the absence VEGFs and other supplements for 8 h. After trypsinization, cells were resuspended in medium containing Ramucirumab (5 µg/mL; Eli Lilly, Indianapolis, Ind.), anti-VEGFR2 monoclonal antibody (20 µg/mL; R2C7-1 or R2C9-11) in the presence of 2 µg/mL VEGF-$A_{165}$ or VEGF-C (Cys156Ser) (R&D; McKinley Place, Nebr.) as indicated, and followed by seeding onto the pre-coated wells for 4 h or 10 h at 37° C. for LEC or HUVEC, respectively. The whole image of each well was pictured using the NIKON Digital Slight DS-U3 system (Tokyo, Japan), and the total number of branch nodes, meshes, and length of tubes formed were quantified by Angiogenesis Analyzer of Image J. Data were represented as means±S.E. in triplicates.

(5) Flow Cytometry Analysis

Cells were washed with phosphate-buffered saline (PBS), dissociated with 2 mM PBS-based EDTA and collected by centrifugation. To block non-specific binding, cells were incubated with PBS containing 1% bovine serum albumin (BSA) for 1 h at 4° C. After PBS wash, HUVEC or HEK293T cells expressing VEGFR2 ($1 \times 10^5$/reaction) were treated with 2 µg/mL anti-VEGFR2 mAbs (R2C7-1 or R2C9-11), Ramucirumab (Eli Lilly, Indianapolis, Ind.) or their isotype-control immunoglobin G (IgG) (BioLegend, San Diego, Calif.) for additional 1 h at 4° C. For detection of VEGFR3 expression, LEC or HEK293T cells expressing VEGFR3 were immuno-probed with antibody against VEGFR3 (Santa Cruz, Dallas, Tex.) or rabbit IgG control (Abcam, Burlingame, Calif.) for 1 h at 4° C. After extensive washing with 1% BSA-containing PBS, cells were stained with their corresponding secondary antibodies, 4 µg/mL goat-anti-mouse IgG conjugated with PE (Biolegend), donkey-anti-rabbit IgG conjugated with FITC (Abcam), or mouse-anti-human IgG conjugated with PE (Biolegend), for 1 h at 4° C. Subsequently, cells were washed and then resuspended in PBS plus 1% paraformaldehyde and 1% BSA. The cell-surface expression of VEGFR2 and VEGFR3 was analyzed using BD FACSCalibur™ flow cytometer (Becton Dickinson, Franklin Lakes, N.J.).

(6) In Situ Proximity Ligation Assay (PLA)

Blockade of VEGFR2 and VEGFR3 homo-/hetero-dimerization by the anti-VEGFR2 (R2C7-1 and R2C9-11) mAbs was investigated using the Duolink in-situ PLA kit (Sigma-Aldrich, St. Louis, Mo.) according to manufacturer's instructions. Briefly, LECs were seeded in 8-well chamber slides and cultured with serum-free medium in the presence of R2C7-1, R2C9-11, or Ramucirumab (Eli Lilly) for 16 h. After, cells were stimulated with VEGF-C (500 ng/mL for 15 min), VEGF-C (Cys156Ser) (2 µg/mL for 10 min) or VEGF-$A_{165}$ (50 ng/ml for 5 min). Cells were washed with PBS, fixed with 4% paraformaldehyde for 15 min and blocked with Blocking buffer (Sigma-Aldrich) for 30 min at RT. Cells stained with commercially available antibody against 2 µg/mL VEGFR2 or VEGFR3 (Santa Cruz, Dallas, Tex.) served as controls. Corresponding species-specific secondary antibody, anti-rabbit PLUS or anti-mouse-MINUS (Sigma-Aldrich), linked to specific oligonucleotides (PLA probes) were added. Ligation of PLA probe reactions was done by adding a solution containing ligase (final concentration 1 unit/µL; Sigma-Aldrich) at 37° C. for 30 min. Signal amplification took place in polymerase-containing solution (10 units/µL; Sigma-Aldrich) by rolling circle amplification of ligated PLA probes at 37° C. for 100 min. After washing with Buffer B (Sigma-Aldrich), slides were stained with DAPI to visualize cell nuclei and mounted with Duolink in-situ mounting medium (Sigma-Aldrich). In addition, isotype-control IgG was used as control. The fluorescent signals (or dots) were imaged and analyzed by MetaMorph Offline software.

(7) Co-Immunoprecipitation Analysis

To determine the inhibitory effect on VEGF-C-induced receptor dimerization by the anti-VEGFR2 antibodies, LEC cells were seeded on 6 cm-diameter dishes until they reached to 70-80% confluency. Cells were washed and starved with serum-free medium containing 20 µg/mL of antibodies (R2C7-1, R2C9-11, or isotype-control antibody) for 16 h. Subsequently, cells were stimulated with or without VEGF-C (500 ng/mL) for 15 min, washed twice with ice-cold PBS and harvested by RIPA buffer (20 mM Tris-HCl (pH 7.5)/150 mM NaCl/1 mM Na/EDTA/1 mM EGTA/ 1% NP-40/1% sodium deoxycholate/2.5 mM sodium pyrophosphate/1 mM β-glycerophosphate/1 mM $Na_3VO_4$/1 µg/mL leupeptin. For immunoprecipitation, lysates (1 mg/sample) were precleared for 2 h with Protein-A/G-agarose beads (Thermo Fisher; Waltham, Mass.) to minimize unspecific binding, and then incubated with anti-VEGFR3 antibody (1 µg/sample, Santa Cruz) with continuous rotation overnight at 4° C. The immunoprecipitated proteins were resolved by native polyacrylamide gel electrophoresis, immunoblotted with commercial-available VEGFR3 antibody (Santa Crus) and visualized using the ECL Western blotting system (Thermo Scientific), as described in the followings.

(8) Native Gel Electrophoresis

Receptor dimerization status of VEGFR2 and VEGFR3 was also measured by native gel electrophoresis (PAGE). Cells were starved with serum-free medium containing 20 µg/mL of R2C7-1 or R2C9-11 for 16 h. Ramucirumab and isotype-control antibody were used as positive and negative controls, respectively. Cells were stimulated with VEGF-C (500 ng/ml) for 15 min and harvested by a hypotonic lysis buffer (20 mM Tris-HCl, pH 7.4; 10 mM NaCl and 1 mM PMSF). Equal amount of sample proteins was mixed with 4× native sample buffer (400 mM Tris-HCl, pH7.5; 40% glycerol and 0.02% bromophenol blue) and the resolved by native PAGE using pre-casted native PAGE gels (Bio-Rad). The dimerization and the phosphorylation statuses of VEGFRs were detected by anti-VEGFR2 (Santa Cruz), anti-VEGFR3 (Santa Cruz) or anti-p-VEGFR3 antibodies (Cell Applications; San Diego, Calif.).

(9) Western Blotting Analysis

Protein lysates were obtained using lysis buffer (20 mM of Tris-HCl pH 8.0/2 mM EDTA/1 mM $Na_3VO_4$/10% glycerol/1% Triton X-100/protease) with addition of phosphatase inhibitor cocktail (Sigma-Aldrich) or RIPA buffer, as indicated. HUVEC and LEC cells were seeded a day before treatments. An anti-VEGFR2 antibody, R2C7-1 or R2C9-11 (5, 10, 20 µg/mL, as indicated), was added into media and incubated at 37° C. for 10 min, followed by stimulation of 20 ng/mL VEGF-$A_{165}$ (R&D) for HUVEC. LEC cells were pre-incubated with the R2C7-1 or R2C9-11 antibody (20 µg/mL), stimulated with VEGF-C (500 ng/mL for 15 min), VEGF-C (Cys156Ser) (2 µg/mL for 10 min) or VEGF-$A_{165}$ (50 ng/mL for 5 min) (R&D), and then harvested by RIPA buffer. Ramucirumab (5 µg/mL; Eli Lilly) and 20 µg/mL appropriate isotype-control IgG (mouse IgG for R2C7-1 and R2C9-11 from Biolegend; rabbit IgG for VEGFR3 antibody from Abcam) served as positive or negative controls, respectively. The concentration of extracted proteins was measured by the Bradford protein assay (Bio-Rad). Equal amounts of total protein (50 µg/sample) were resolved on a 12% sodium dodecyl sulfate-polyacrylamide gel (Bio-Rad). Proteins were transferred to a nitrocellulose membrane (Hybond™-P; Amersham Biosciences, Piscataway, N.J.). After blocking with blocking buffer (3% BSA/0.1% Tween-20 in TBS) for 2 h at RT, the membranes were incubated with primary antibodies for anti-VEGFR2 (Santa Cruz), -VEGFR3 (Santa Cruz), p-VEGFR3 (Tyr1230/1231) (Cell applications), p-FAK, p-p38ERK (Cell Signaling; Danvers, Mass.) and antibody against 13-Actin (MilliporeSigma; Burlington, Mass.) or tubulin at 4° C. overnight, followed by incubation with appropriate secondary antibodies linked to horseradish peroxidase. Immunoreactive proteins were visualized using the SuperSignal West Pico chemiluminescence (Thermo Scientific), and the signals were detected on X-ray film (FUJI; Tokyo, Japan).

(10) Cell-Based Competitive ELISA

The epitopes of R2C7-1 and R2C9-11 anti-VEGFR2 antibodies were determined by cell-based competitive ELISA. HEK293T cells expressing VEGFR2 or VEGFR3 were seeded onto 96-well plates at a density of 50000 cells/100 µL/well and incubated overnight at 37° C. After extensive wash, cells were fixed with 1% glutaraldehyde in PBS, and then washed with 0.1% Tween-20 in PBS (PBST) three times. For reducing non-specific binding, the cells were blocked with 3% BSA-containing PBS at 37° C. for 30 min. On the other hand, the R2C7-1 and R2C9-11 antibodies (8 µg/well) were absorbed with an indicated dose (0.2, 1.0, or 5.0 µg/well) of individual immunoglobin-like domains (IgD4, D5, D6 and D7) of the VEGFR2 or VEGFR3 recombinant proteins at 37° C. for 30 min. Cells expressing VEGFR2 or VEGFR3 were subsequently incubated with the pre-absorbed R2C7-1 or R2C9-11 antibodies for 1 h at 37° C., and followed by extensive PBST wash for three times. The bound antibodies were probed with goat-anti-mouse IgG conjugated with HRP for 1 h at 37° C., visualized by addition of ABTS (37° C. for 30 m) and measured by the SpectraMax M5 microplate reader (Molecular Device; San Jose, Calif.) at $OD_{405}$.

(11) Gene Construct and Expression

The extracellular immunoglobin (Ig) domains of VEGFR2 were constructed into pGEX-4T-1 plasmid (GE Healthcare; Chicago, Ill.), and the recombinant protein was expressed in the competent E. coli cells system. The extracellular Ig domain and its subdomains 6 and 7 of VEGFR2 gene (NM_002253.2) was generated by gene-specific PCR primers using the plasmid EX-I0114-Lv205 (GeneCopoeia; Rockville, Md.) as template, restrictedly digested with BamH1 and XhoI (NEB; Ipswich, Mass.) and cloned into pGEX-4T-1 vector (GE Healthcare; Chicago, Ill.), which was named VEGFR2-ED Ig D1-7 and D6-7, respectively. The gene construct was transformed into JM109 cells (Promega; Madison, Wis.) by heat shock at 42° C. for 40 sec and selected by Ampicillin (50 µg/mL) on LB agar. The gene insert in antibiotic-resistant cells were confirmed by a standard colony PCR and gene sequencing. The positive cells were grown in the Ampicillin-containing LB broth and induced for protein expression by 1 mM IPTG (Sigma-Aldrich) at 37° C. for 3 h. The cells were pelleted, suspected in ice-cold Lysis buffer (10 mM Tris-HCl pH8.0/0.15 M NaCl/1 mM EDTA) with addition of 100 µg/mL lysozyme, 10 mM PMSF and 5 units of benzonase (Sigma-Aldrich). After sonication, the soluble fraction was obtained by centrifugation at 10,000×g for 30 min. The GST-tagged recombinant proteins were captured with glutathione-conjugated Sepharose beads (Sigma-Aldrich), eluted with 10 mM reduced-form glutathione and dialyzed against PBS overnight. The purity of the recombinant proteins was examined by SDS-PAGE.

For expressing the extracellular domain of VEGFR3 gene in eukaryotic cells, the gene inserts were cloned into the pCMV6-XL6-myc vector (OriGene; Rockville, Md.) for protein expression. In brief, the extracellular Ig domains and its subdomains of VEGFR3 gene (NM_002020.4) were generated by PCR using gene-specific primers and pCMV6-XL6-VEGFR3 (a kind gift from Dr. J. L. Su) as template. After restrict digestion, the inserts were cloned into the EcoRI and Xbal sites of the pCMV6-XL6 (OriGene; Rockville, Md.) and transformed into DH5a cells (Thermo Scientific) for gene amplification. Gene sequences of the resultant VEGFR3-ED Ig D1-7-, D3-4-, and D6-7-myc plasmids were verified by direct sequencing.

To express and purify recombinant proteins encoded by the mentioned plasmids, HEK293 cells were transfected with Turbofect transfection reagent (Thermo Scientific), as described in manufacture's instruction. The encoded proteins were purified with anti-Myc antibody-mobilized columns, resolved in native-PAGE gels using Native PAGE Novex Bis-Tris gel system (Invitrogen; Carlsbad, Calif.) and followed by immunoblotting on nitrocellulose membrane. To examine the cross-reactivity of the VEGFR2 antibodies, the blots were probed with R2C7-1 or R2C9-11 antibody and detected by goat-anti-mouse IgG-HRP (Santa Cruz). The signal was visualized using the SuperSignal West Pico chemiluminescence (Thermo Scientific).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

---

What is claimed is:

1. An isolated antibody, comprising heavy chain complementary determining regions CDR1, CDR2, and CDR3 from a heavy chain variable region sequence having SEQ ID NO: 1; and light chain complementary determining regions CDR1, CDR2, and CDR3 from a light chain variable region sequence having SEQ ID NO: 2; wherein the antibody binds specifically to both vascular endothelial growth factor receptor-2 (VEGFR2) and vascular endothelial growth factor receptor-3 (VEGFR3).

2. The isolated antibody of claim 1, wherein the antibody has a heavy chain variable region sequence that is at least 80% identical to SEQ ID NO: 1, and a light chain variable region sequence that is at least 80% identical to SEQ ID NO: 2.

3. The antibody of claim 2, wherein the antibody is an antibody that contains an Fc region, an Fab fragment, an Fab' fragment, an F(ab')2 fragment, a single-chain antibody, an scFV multimer, a monovalent antibody, a multispecific antibody, or a chimeric antibody.

4. The isolated antibody of claim 1, wherein the heavy chain CDR1, CDR2, and CDR3, respectively, have SEQ ID NOs: 5, 6, and 7 or SEQ ID NOs: 8, 9, and 7, and wherein the light chain CDR1, CDR2, and CDR3, respectively, have SEQ ID NOs: 10, 11, and 12.

5. The antibody of claim 4, wherein the antibody is an antibody that contains an Fc region, an Fab fragment, an Fab' fragment, an F(ab')2 fragment, a single-chain antibody, an scFV multimer, a monovalent antibody, a multispecific antibody, or a chimeric antibody.

6. The antibody of claim 1, wherein the antibody is an antibody that contains an Fc region, an Fab fragment, an Fab' fragment, an F(ab')2 fragment, a single-chain antibody, an scFV multimer, a monovalent antibody, a multispecific antibody, or a chimeric antibody.

7. The antibody of claim 1, wherein the antibody is a humanized antibody.

8. A pharmaceutical composition comprising the antibody of claim 1 and a pharmaceutically acceptable carrier.

9. An antibody conjugate, comprising the antibody of claim 1 and another molecule.

10. A method of inhibiting homodimerization of VEGFR2 and/or VEGFR3 or heterodimerization of VEGFR2 and VEGFR3 in a cell, comprising contacting the cell with the antibody of claim 1.

11. A method of inhibiting VEGFR2 and/or VEGFR3 signaling in a cell, comprising contacting the cell with the antibody of claim 1.

12. A method of inhibiting angiogenesis and/or lymphangiogenesis in a subject in need thereof, comprising administering to the subject an effective amount of the antibody of claim 1.

13. A method of treating a solid tumor in a subject in need thereof, comprising administering to the subject an effective amount of the antibody of claim 1.

14. The method of claim 13, wherein the solid tumor is selected from the group consisting of bladder cancer, breast cancer, cervical cancer, colon cancer, rectal cancer, kidney cancer, liver cancer, skin cancer, mesothelioma, lung cancer, oral cancer, ovarian cancer, pancreatic cancer, prostate cancer, sarcoma, and thyroid cancer.

15. The method of claim 13, further comprising administering another therapeutic agent to the subject.

16. A method of detecting VEGFR2 and/or VEGFR3 or a fragment thereof in a biological sample, comprising:
 contacting the sample with the antibody of claim 1;
 assaying for specific binding between the antibody and VEGFR2 and/or VEGFR3 or a fragment thereof; and
 detecting the VEGFR2 and/or VEGFR3 or a fragment thereof in the sample based on the specific binding.

* * * * *